(12) United States Patent
Kitagawa et al.

(10) Patent No.: US 11,134,852 B2
(45) Date of Patent: Oct. 5, 2021

(54) PRESSURE PULSE WAVE DETECTOR AND BIOMETRIC INFORMATION MEASUREMENT DEVICE

(71) Applicant: OMRON HEALTHCARE CO., LTD., Kyoto (JP)

(72) Inventors: Tsuyoshi Kitagawa, Muko (JP); Shingo Yamashita, Muko (JP); Hiroyuki Kinoshita, Muko (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 411 days.

(21) Appl. No.: 16/158,465

(22) Filed: Oct. 12, 2018

(65) Prior Publication Data
US 2019/0046048 A1 Feb. 14, 2019

Related U.S. Application Data

(63) Continuation of application No. PCT/JP2017/012940, filed on Mar. 29, 2017.

(30) Foreign Application Priority Data

Apr. 14, 2016 (JP) .............................. JP2016-081392

(51) Int. Cl.
*A61B 5/02* (2006.01)
*A61B 5/0225* (2006.01)
(Continued)

(52) U.S. Cl.
CPC .............. *A61B 5/0225* (2013.01); *A61B 5/02* (2013.01); *A61B 5/02108* (2013.01);
(Continued)

(58) Field of Classification Search
CPC .......... A61B 5/02108; A61B 2562/046; A61B 2562/066; A61B 5/6843; A61B 5/02116;
(Continued)

(56) References Cited

U.S. PATENT DOCUMENTS

| 4,830,017 A | 5/1989 | Perry et al. |
| 5,238,000 A * | 8/1993 | Niwa ................. A61B 5/02255 600/485 |

(Continued)

FOREIGN PATENT DOCUMENTS

| CN | 1517063 | 8/2004 |
| CN | 1969745 | 5/2007 |

(Continued)

OTHER PUBLICATIONS

Hashimoto Masao, Kobayashi Hideyuki, Sato Hironori; English Translation of "Pulse Wave Measuring Apparatus", Apr. 9, 2009, Japanese Patent Office, Translation obtained from Japan Platform for Patent Information. (Year: 2009).*

(Continued)

*Primary Examiner* — Christian Jang
(74) *Attorney, Agent, or Firm* — Wenderoth, Lind & Ponack, L.L.P.

(57) ABSTRACT

A pressure pulse wave detector includes: a pressing member which includes a pressing face in which element arrays each including pressure detecting elements arranged in one direction are arranged in a direction intersecting with the one direction; a pressing mechanism which presses the pressing face against a body surface of a living body; a rotation driving mechanism which rotates the pressing face around each of two axes which are perpendicular to a pressing direction of the pressing face pressed by the pressing mechanism and include a first axis extending in the one direction and a second axis perpendicular to the one direction; a support member which supports the pressing mechanism, the rotation driving mechanism and the pressing member; a housing which houses therein the support member; and a movement mechanism which moves the support member in the one direction inside the housing.

3 Claims, 18 Drawing Sheets

(51) Int. Cl.
  *A61B 5/00* (2006.01)
  *A61B 5/021* (2006.01)
  *A61B 5/0245* (2006.01)
(52) U.S. Cl.
  CPC ...... *A61B 5/02116* (2013.01); *A61B 5/02141* (2013.01); *A61B 5/6824* (2013.01); *A61B 5/6843* (2013.01); *A61B 5/0245* (2013.01)
(58) Field of Classification Search
  CPC . A61B 5/0225; A61B 5/02141; A61B 5/6824; A61B 5/0245
  See application file for complete search history.

(56) References Cited

U.S. PATENT DOCUMENTS

| | | | |
|---|---|---|---|
| 6,676,600 B1 * | 1/2004 | Conero | A61B 5/00 600/438 |
| 2004/0193060 A1 | 9/2004 | Hashimoto et al. | |
| 2010/0185104 A1 | 7/2010 | Kim et al. | |
| 2017/0367649 A1 * | 12/2017 | Kitagawa | A61B 5/02108 |

FOREIGN PATENT DOCUMENTS

| | | |
|---|---|---|
| JP | 1-288228 | 11/1989 |
| JP | 2-1220 | 1/1990 |
| JP | 5-20709 | 3/1993 |
| JP | 5-184548 | 7/1993 |
| JP | 2002-330932 | 11/2002 |
| JP | 2004-215752 | 8/2004 |
| JP | 2004-305268 | 11/2004 |
| JP | 2008-12161 | 1/2008 |
| JP | 2009-072407 | 4/2009 |
| JP | 2009072407 A * | 4/2009 |
| JP | 2010-220948 | 10/2010 |
| JP | 2010-220949 | 10/2010 |
| WO | 01/17425 | 3/2001 |

OTHER PUBLICATIONS

International Search Report dated Jun. 27, 2017 in International (PCT) Application No. PCT/JP2017/012940.
Written Opinion of International Searching Authority dated Jun. 27, 2017 in International (PCT) Application No. PCT/JP2017/012940.
International Preliminary Report on Patentability dated Aug. 30, 2017 in International (PCT) Application No. PCT/JP2017/012940.
Office Action dated Sep. 11, 2020 in corresponding Chinese Application No. 201780023406.3, with English Translation.
Extended European Search Report dated Sep. 25, 2019 in corresponding European Patent Application No. 17782243.4.

* cited by examiner

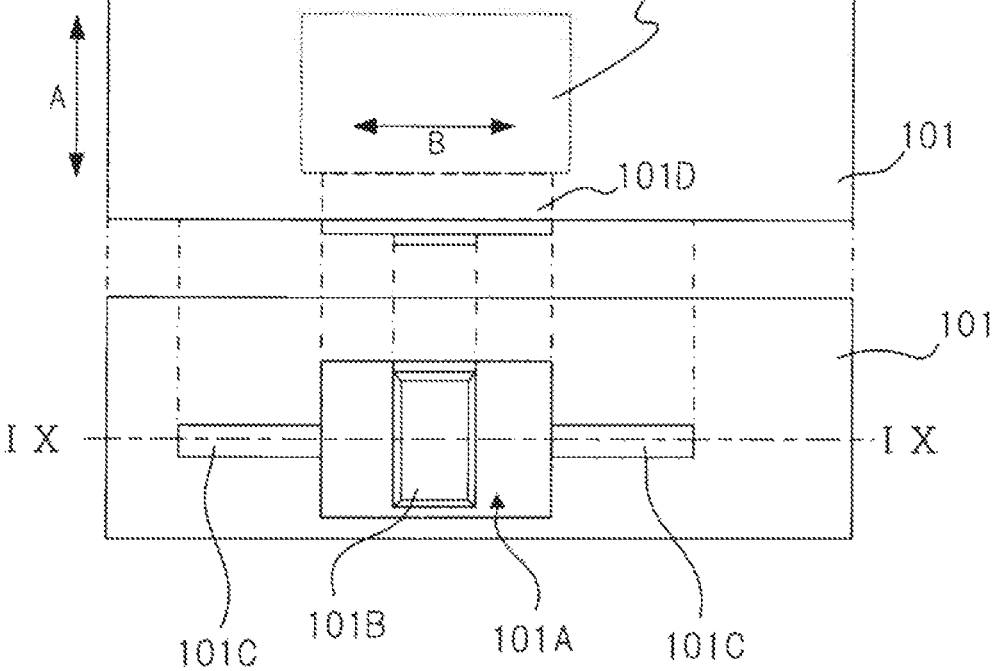

FIG.16
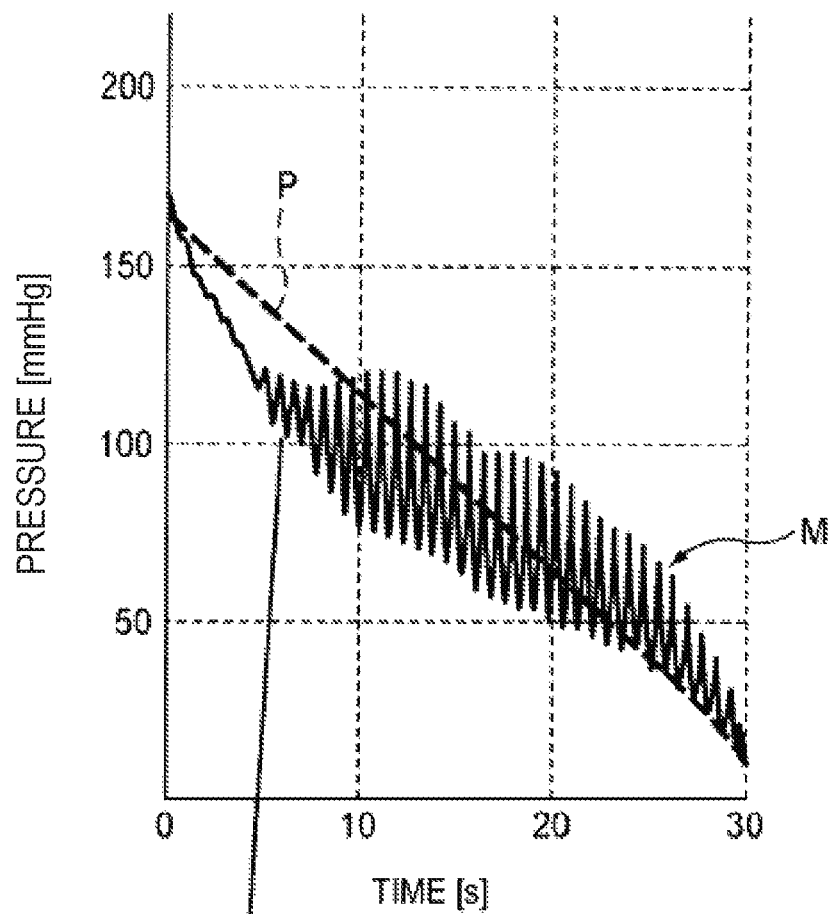
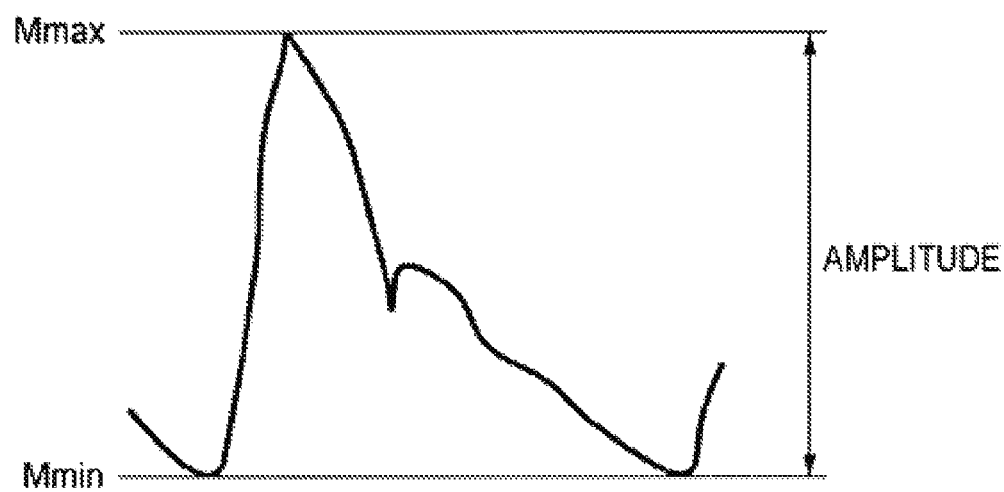

PRESSURE PULSE WAVE DETECTOR AND BIOMETRIC INFORMATION MEASUREMENT DEVICE

CROSS-REFERENCE TO RELATED APPLICATIONS

This is a Continuation of International Patent Application No. PCT/JP2017/012940 filed Mar. 29, 2017, which claims the benefit of Japanese Patent Application No. 2016-081392 filed Apr. 14, 2016. The disclosures of the prior applications are hereby incorporated by reference herein in their entireties.

TECHNICAL FIELD

Aspects of the present invention relate to a pressure pulse wave detector and a biometric information measurement device.

BACKGROUND ART

There has been known a biometric information measurement device that can measure biometric information such as blood pressure, a pulse rate or a heart rate using information detected by a pressure sensor in a state where the pressure sensor is brought into direct contact with a living body part through which an artery such as a radial artery of a wrist passes. In the biometric information measurement device, a positional relation between the pressure sensor and the artery affects detection accuracy of pressure pulse waves. Accordingly, configurations for positional adjustment between a living body part and a pressure sensor have been proposed, as shown in the Patent Literature 1 (JP-A-2010-220948), Patent Literature 2 (JP-A-2010-220949), Patent Literature 3 (JP-A-H02-001220), Patent Literature 4 (JP-A-2002-330932) and Patent Literature 5 (JP-A-H01-288228).

A biometric information measuring device described in Patent Literature 1 has a sensor group including forty-two sensors that are arranged in a matrix of 6×7 so as to be brought into contact with a living body part. In order to make an output of each of the sensors of the sensor group excellent, a mechanism that can manually adjust a slope of the sensor group in an artery direction is provided.

A biometric information measurement device described in Patent Literature 2 has a sensor group including forty-two sensors that are arranged in a matrix of 6×7 so as to be brought into contact with a living body part. In order to make the contact of the sensor group follow movement of a hand, the sensor group is divided into four division areas, and a mechanism that can adjust heights of the four division areas individually is provided.

A biometric information measurement device described in Patent Literature 3 has a pressure sensor brought into contact with a living body part, and that has a driving portion moving the pressure sensor in a direction intersecting with an artery.

A biometric information measurement device described in Patent Literature 4 has a pressure sensor array brought into contact with a living body part, and that has a driving portion rotating the pressure sensor array in a plane intersecting with a pressing direction of the pressure sensor array.

A biometric information measurement device described in Patent Literature 5 has a pressing face where pressure sensor arrays to be brought into contact with a living body part are formed to be arranged side by side, and that has a driving portion rotating the pressing face around an axis extending in a direction perpendicular to an array direction of the pressure sensor arrays.

The device described in Patent Literatures 1, 2 can change the contact state of the sensor group with the living body part. However, the contact state changes following the shape of a wrist of a user or the contact state is changed manually. Therefore, the device described in Patent Literatures 1, 2 cannot perform positioning of the sensors for which detection accuracy of pulse waves has been sufficiently taken into consideration.

The device described in Patent Literatures 3, 4, 5 drives the position of each pressure sensor so as to make the output of the pressure sensor excellent. Accordingly, the device described in Patent Literatures 3, 4, 5 can perform positioning of the pressure sensor in consideration of detection accuracy of pulse waves. However, when the pressure sensor is pressed onto the living body part and biometric information is measured using information outputted from the pressure sensor in this state, it is assumed that the position of the artery changes due to pressing force. The device described in Patent Literatures 3, 4 or 5 however has difficulty in following such a position change sufficiently.

SUMMARY

Embodiments of the present invention address the above disadvantages and other disadvantages not described above. However, the present invention is not required to overcome the disadvantages described above, and thus, an exemplary embodiment of the present invention may not overcome any of the problems described above.

A pressure pulse wave detector according to an embodiment of the present invention includes: a pressing member which includes a pressing face in which element arrays each including pressure detecting elements arranged in one direction are arranged in a direction intersecting with the one direction; a pressing mechanism which is configured to press the pressing face against a body surface of a living body in a state where the one direction intersects with an extension direction of an artery under the body surface; a rotation driving mechanism which is configured to rotate the pressing face around each of two axes which are perpendicular to a pressing direction of the pressing face pressed by the pressing mechanism and include a first axis extending in the one direction and a second axis perpendicular to the one direction; a support member which supports the pressing mechanism, the rotation driving mechanism and the pressing member; a housing which houses therein the support member; and a movement mechanism which is configured to move the support member in the one direction inside the housing.

A biometric information measurement device according to an embodiment of the present invention includes: the above pressure pulse wave detector; and a biometric information calculating portion which is configured to calculate biometric information based on pressure pulse waves detected by the pressure detecting elements included in the pressure pulse wave detector.

BRIEF DESCRIPTION OF DRAWINGS

The above and other aspects of the present invention will become more apparent and more readily appreciated from the following description of embodiments of the present invention taken in conjunction with the attached drawings.

FIGS. 8A to 8C are views schematically illustrating the vicinity of a portion of a housing 101 shown in FIG. 1 in which the pressure pulse wave detecting portion 100 is housed therein.

FIG. 16 shows graphs illustrating a change of the pressing force on the wrist and an example of a change in pressure pulse waves detected by a most suitable pressure detecting element.

DESCRIPTION OF EMBODIMENT

Hereinafter, embodiments of the present invention will be described with reference to the drawings.

Figure 1:
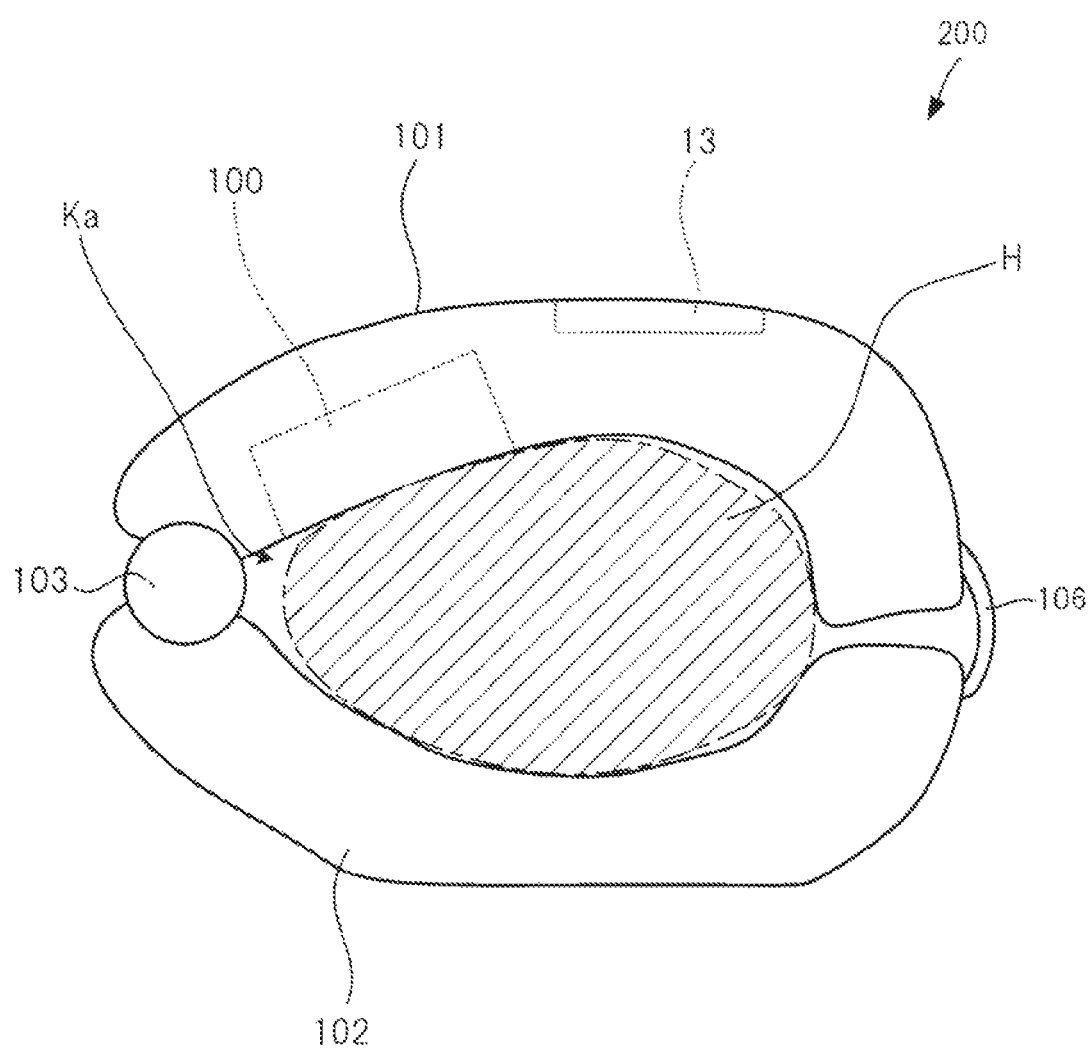
FIG. 1 is a side view illustrating a schematic configuration of a biometric information measurement device 200 for explaining an embodiment of the present invention.

FIG. 1 is a side view illustrating a schematic configuration of a biometric information measurement device 200 for explaining an embodiment of the present invention. The biometric information measurement device 200 shown in FIG. 1 is a wrist-attached type biometric information measurement device that is attached to a wrist of a measurement subject, where a radial artery is present. The biometric information measurement device 200 is not limited to the wrist-attached type but any type may be used as long as it can be attached on a part of a living body where an artery is present under the body surface.

The biometric information measurement device 200 includes a body portion and a belt 106. The body portion is constituted by a housing 101, a housing 102, and a hinge portion 103 that couples the housing 101 and the housing 102 to each other. The belt 106 is provided for fixing the body portion to the wrist. By the hinge 103, the housing 102 is rotatably coupled to the housing 101.

Inner circumferential surfaces of the housings 101 and 102 are formed into a shape following an external shape of the wrist H. In a state where an opposite-side end portion of the housing 101 to the hinge portion 103 is brought nearest to the housing 102, a space Ka into which the wrist H of the measurement subject can be inserted is formed between the housing 101 and the housing 102.

In a state where the wrist H is inserted into the space Ka, one end of the housing 101 and one end of the housing 102 are fixed to each other by the belt 106. Thus, the biometric information measurement device 200 is fixed to (attached to) the wrist H. Incidentally, the housing 101 and the housing 102 may be integrated without interposition of the hinge portion 103 therebetween.

The housing 101 includes a pressure pulse wave detecting portion 100 and a display portion 13. The pressure pulse wave detecting portion 100 is provided at a position facing the wrist H in the state where the biometric information measurement device 200 is attached to the wrist H. In this state, the display portion 13 is provided in an outer circumference surface of the housing 101. A pressure pulse wave detector is constituted by the housing 101 and the pressure pulse wave detecting portion 100.

Figure 2:
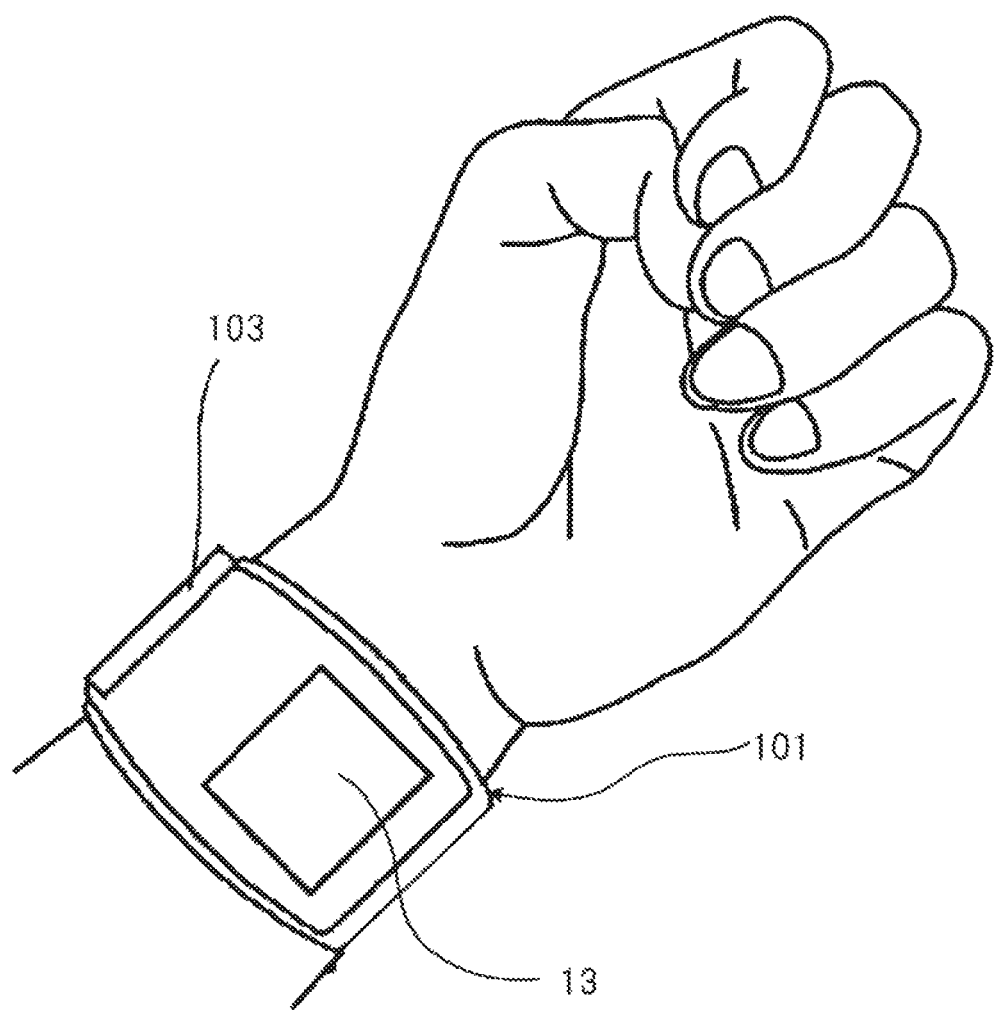
FIG. 2 is a view of a state where the biometric information measurement device 200 shown in FIG. 1 is attached to a wrist, as seen from a palm side of a hand.
Figure 3:
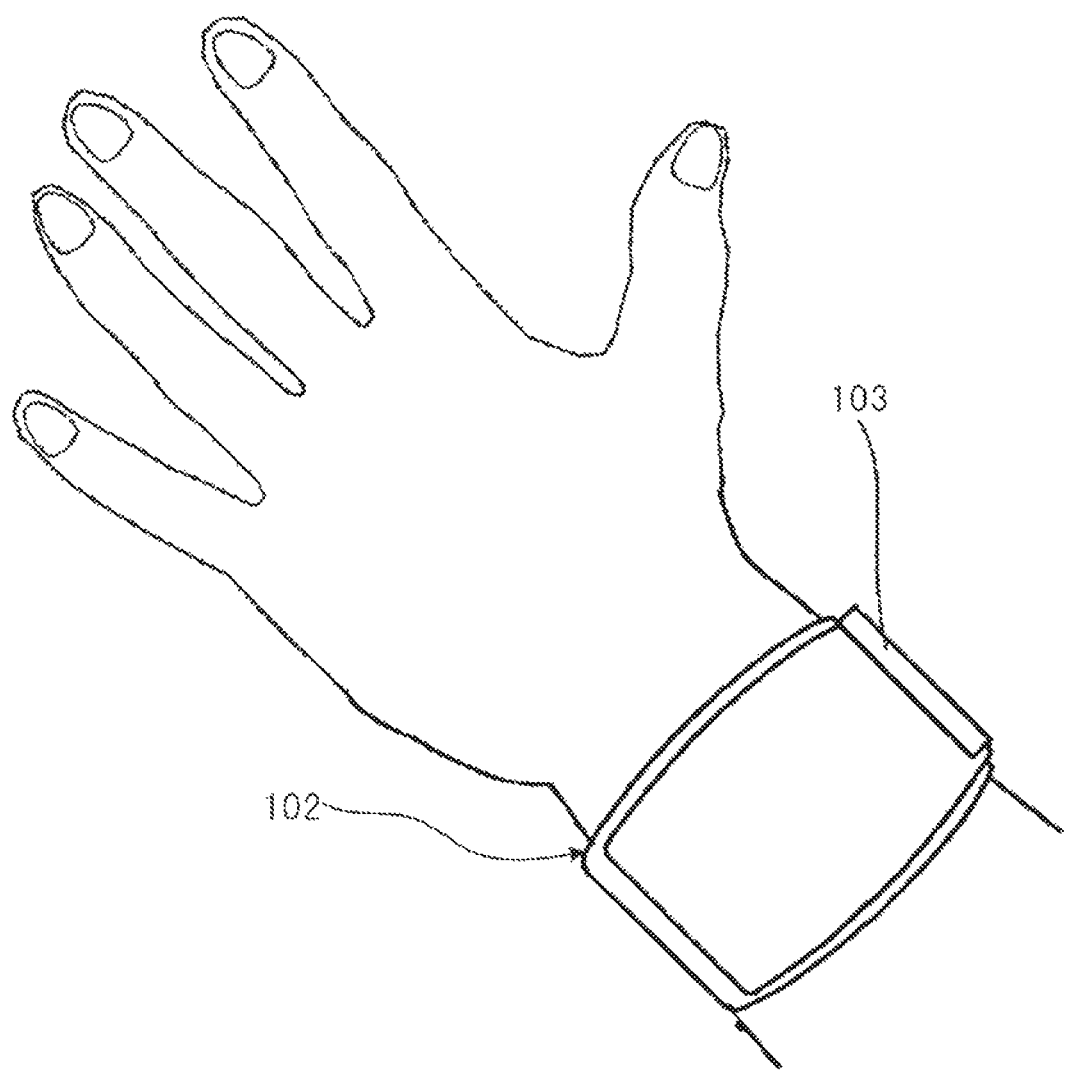
FIG. 3 is a view of the state where the biometric information measurement device 200 shown in FIG. 1 is attached to the wrist, as seen from a back side of the hand.

FIG. 2 is a view of a state where the biometric information measurement device 200 is attached to a left wrist of a measurement subject, as seen from a palm side of the hand. As shown in FIG. 2, the display portion 13 is provided in the outer circumferential surface of the housing 101, and the display portion 13 can be visually recognized from the palm side of the hand. FIG. 3 is a view of the state where the biometric information measurement device 200 is attached to the left wrist of the measurement subject, as seen from a back side of the hand.

Figure 4:
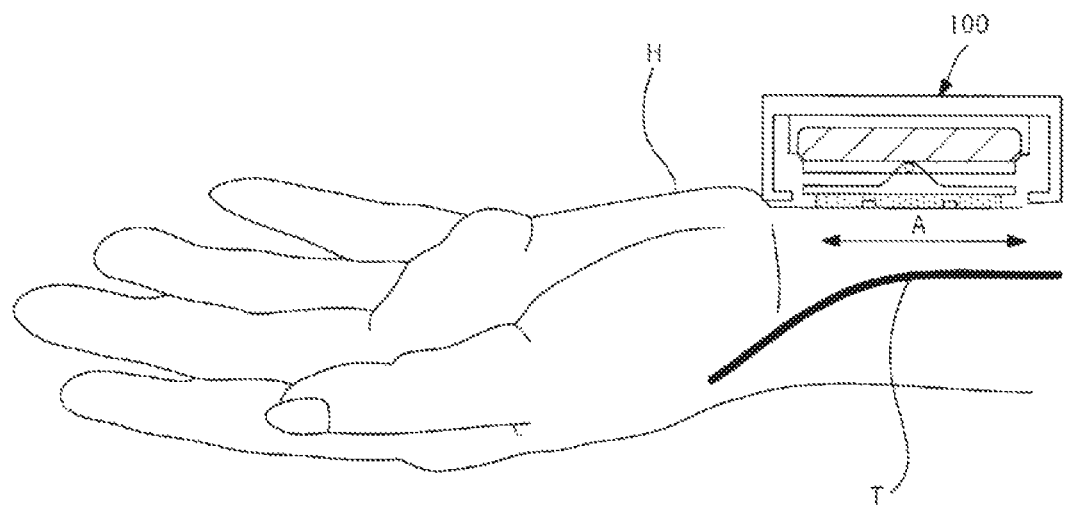
FIG. 4 is a sectional schematic view illustrating a schematic configuration of a pressure pulse wave detecting portion 100 in the state where the biometric information measurement device 200 shown in FIG. 1 is attached to the wrist.

FIG. 4 is a sectional schematic view showing the configuration of the pressure pulse wave detecting portion 100 in the state where the biometric information measurement device 200 is attached to the wrist as shown in FIGS. 2 and 3. Only the pressure pulse wave detecting portion 100 in the biometric information measurement device 200 is illustrated in FIG. 4.

Figure 5:
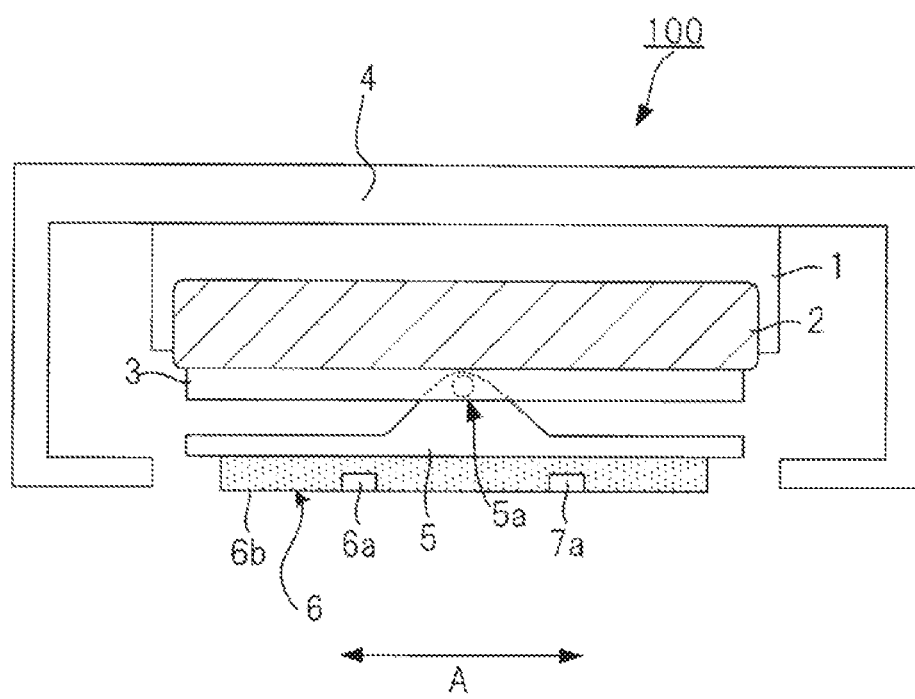
FIG. 5 is an enlarged view of the pressure pulse wave detecting portion 100 shown in FIG. 4.
Figure 6:
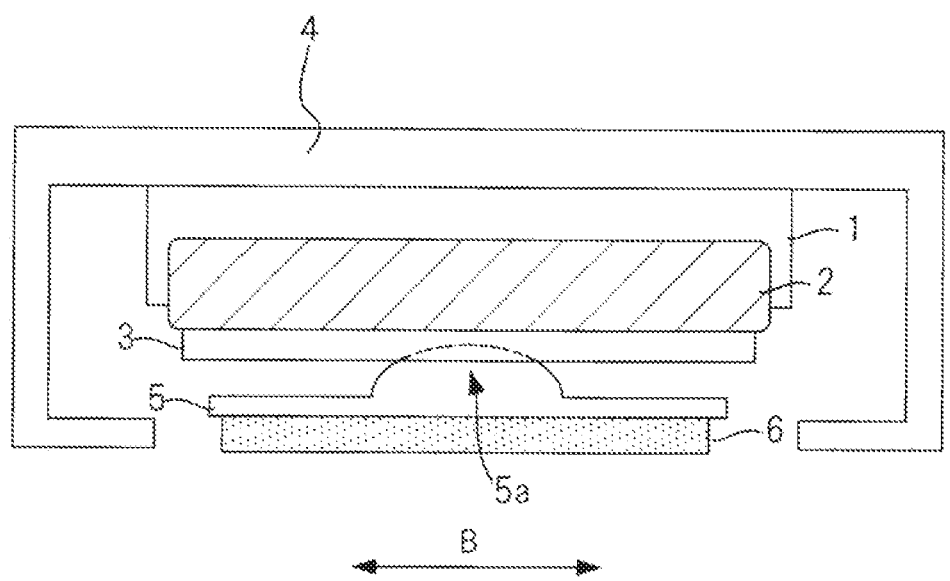
FIG. 6 is a sectional schematic view of the pressure pulse wave detecting portion 100 in the attached state shown in FIG. 4, as seen from a finger side.
Figure 7:
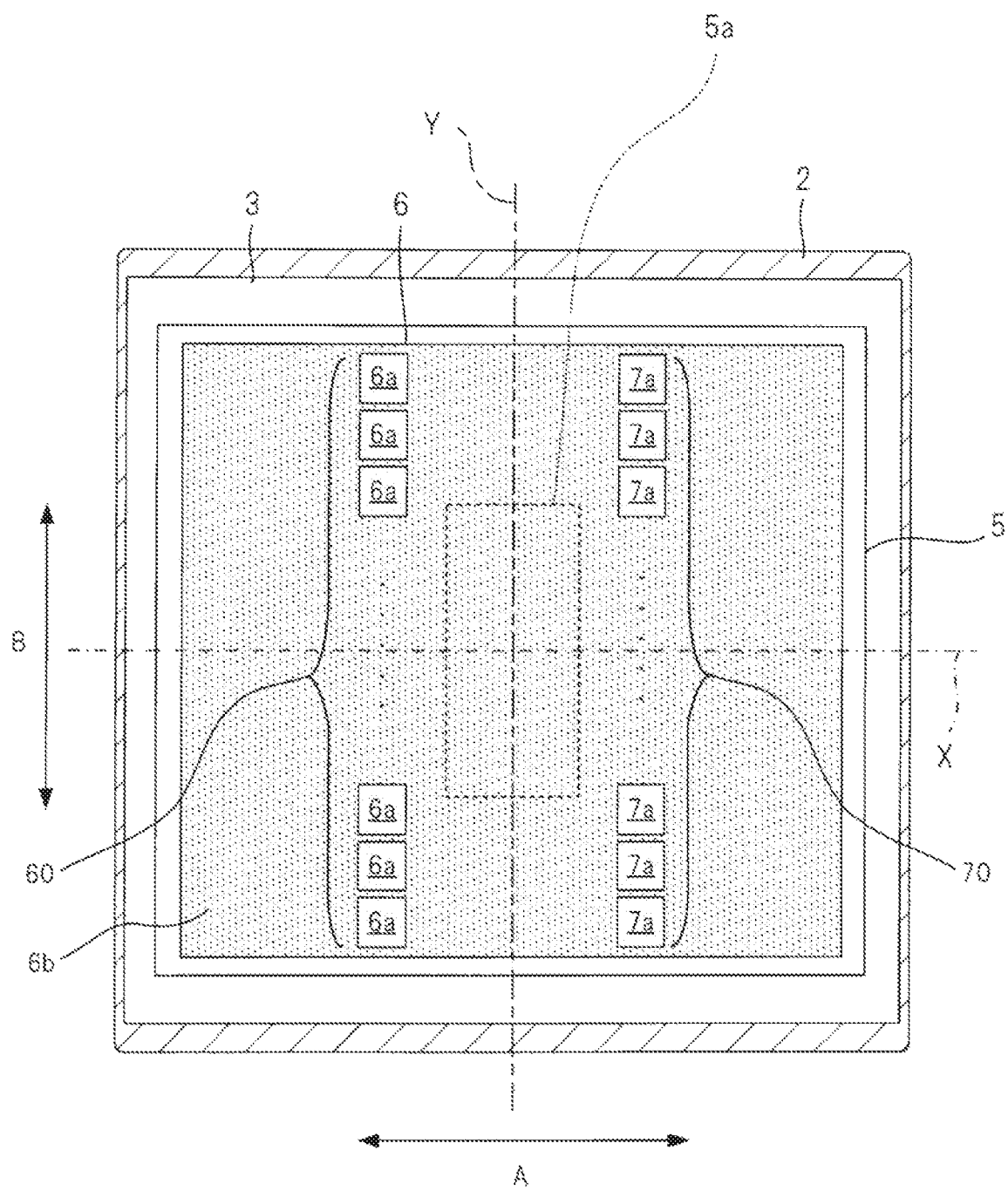
FIG. 7 is a view of the pressure pulse wave detecting portion 100 in the attached state shown in FIG. 4, as seen from a contact region side with the wrist of the pressure pulse wave detecting portion 100.

FIG. 5 is an enlarged view of the pressure pulse wave detecting portion 100 shown in FIG. 4. FIG. 6 is a sectional schematic view of the pressure pulse wave detecting portion 100 in the attached state shown in FIG. 4, as seen from a fingertip side of the measurement subject. FIG. 7 is a view of the pressure pulse wave detecting portion 100 in the attached state shown in FIG. 4, as seen from a contact region side with the wrist of the pressure pulse wave detecting portion 100. FIGS. 4 to 7 schematically illustrate the pressure pulse wave detecting portion 100 but do not limit the dimensions, the layout, or the like of the respective portions.

The pressure pulse wave detecting portion 100 includes a housing 1, a flat plate portion 3, a rotationally moving portion 5, a sensor portion 6, and an accommodating portion 4. An air bag 2 is provided in the housing 1. The flat plate portion 3 is a flat plate-like member fixed to the air bag 2. The rotationally moving portion 5 is supported so as to be rotatable around each of two axes with respect to the flat plate portion 3 by a two-axis rotation mechanism 5a. The sensor portion 6 is provided on an opposite-side flat surface of the rotationally moving portion 5 to the flat plate portion 3 side. The accommodating portion 4 accommodates the housing 1, the air bag 2, the flat plate portion 3, the two-axis rotation mechanism 5a, the rotationally moving portion 5, and the sensor portion 6.

The housing 1, the air bag 2, the flat plate portion 3, and the rotationally moving portion 5 constitute a pressing mechanism that presses a pressing face 6b of the sensor portion 6 against a body surface of the living body part (wrist) in a state where the biometric information measurement device 200 is attached to the wrist. The pressing mechanism is not limited to the mechanism using the air bag but may be any mechanism as long as it can press the pressing face 6b of the sensor 6 against the body surface.

In the air bag 2, an internal air volume is controlled by a pump (not shown). Thus, the flat plate portion 3 fixed to the air bag 2 is moved in a direction perpendicular to a front surface (flat surface on the rotationally moving portion 5 side) of the flat plate portion 3.

In the attached state shown in FIG. 4, the pressing face 6b of the sensor portion 6 included in the pressure pulse wave detecting portion 100 makes contact with the skin of the wrist of the measurement subject. Since the air volume injected into the air bag 2 increases in this state, the internal pressure of the air bag 2 increases so that the sensor portion 6 is pressed toward a radial artery T under the wrist. Description will be made below on the assumption that pressing force toward the radial artery T by the sensor portion 6 is equivalent to the internal pressure of the air bag 2.

As shown in FIG. 7, the sensor portion 6 has an element array 60 and an element array 70. The element array 60 includes a plurality of pressure detecting elements 6a arranged side by side in a direction B intersecting (perpendicularly in the example of FIG. 7) with an extension direction A of the radial artery T present in the attached part, in the attached state shown in FIG. 4. The element array 70 includes a plurality of pressure detecting elements 7a arranged side by side in the direction B. The element array 60 and the element array 70 are arranged side by side in the direction A.

Each pressure detecting element 6a is paired with a pressure detecting element 7a that is in the same position in the direction B as the pressure detecting element 6a. The sensor portion 6 has a configuration in which such pairs are arranged in the direction B. For example, a strain gauge resistance type element, a semiconductor piezoresistance type element, or an electrostatic capacitance type element can be used as each of the pressure detecting elements 6a and the pressure detecting elements 7a.

The respective pressure detecting elements included in the element array 60 and the element array 70 are formed in one and the same flat surface. The flat surface is protected by a protective member formed of a resin or the like. The flat surface in which the respective pressure detecting elements are formed and a front surface of the protective member protecting the flat surface are parallel with each other. The front surface of the protective member forms the pressing face 6b.

The pressure detecting elements 6a (7a) are pressed toward the radial artery T so that the array direction of the pressure detecting elements 6a (7a) intersects (substantially perpendicularly) with the radial artery T. Thus, the pressure detecting elements 6a (7a) detect pressure oscillation waves arising from the radial artery T and transmitted to the skin, i.e. pressure pulse waves. A pressure signal outputted from each of the pressure detecting elements 6a (7a) includes a direct current (DC) component generated due to contact with an object, and an alternating current (AC) component generated due to the pressure vibration wave. The AC component serves as a signal of the pressure vibration wave.

An interval between adjacent ones of the pressure detecting elements 6a (7a) in the array direction is made small enough so that a necessary and sufficient number of the pressure detecting elements 6a (7a) can be disposed on the radial artery T. A length of each of the element arrays 560 and 70 is made necessarily and sufficiently larger than a diameter of the radial artery T. The sensor portion 6 constitutes a pressing member.

As shown in FIG. 7, the two-axis rotation mechanism 5a is a mechanism for rotating the rotationally moving portion 5 around each of two rotation axes X and Y perpendicular to the pressing direction of the flat plate portion 3 pressed by the air bag 2. The two-axis rotation mechanism 5a and the rotationally moving portion 5 constitute a rotation driving mechanism.

The two-axis rotation mechanism 5a has the two rotation axes X and Y that are perpendicular to each other and that are set on the front surface of the flat plate portion 3. The rotation axes X and Y are respectively driven and rotated by a rotation driving portion 10 which will be described later.

The rotation axis Y is a first axis extending in the array direction of the pressure detecting elements 6a (7a) formed in the pressing face 6b. The rotation axis Y is set (in the middle in the example of FIG. 7) between the element array 60 and the element array 70 in the plan view of FIG. 7.

The rotation axis X is a second axis extending in a direction perpendicular to the array direction of the pressure detecting elements 6a (7a) formed in the pressing face 6b. The rotation axis X is set on a straight line by which each of the element array 60 and the element array 70 is halved equally in the example of FIG. 7.

When the rotationally moving portion 5 rotates around the rotation axis X, the pressing face 6b rotates around the rotation axis X. When the rotationally moving portion 5 rotates around the rotation axis Y, the pressing face 6b rotates around the rotation axis Y.

The accommodating portion 4 of the pressure pulse wave detecting portion 100 is housed in the housing 101 and supported by the housing 101 so as to be movable in the direction B. The accommodating portion 4 is constituted, for example, by a cup-like member, and the housing 1, the air bag 2, the flat plate 3, the two-axis rotation mechanism 5a, the rotationally moving portion 5 and the sensor portion 6 are accommodated in a hollow portion of the cup-like member. Specifically, the accommodating portion 4 supports the housing 1 in the hollow portion. Thus, the housing 1, and the air bag 2, the flat plate portion 3, the two-axis rotation mechanism 5a, the rotationally moving portion 5 and the sensor portion 6 that are fixed to the housing 1 move in accordance with movement of the accommodating portion 4.

Any support member can be used as the accommodating portion 4 as long as it can support the pressing mechanism constituted by the housing 1, the air bag 2, the flat plate portion 3 and the rotationally moving portion 5, the rotation driving mechanism constituted by the two-axis rotation mechanism 5a and the rotationally moving portion 5, and the sensor portion 6 so that the pressing mechanism, the rotation driving mechanism, and the sensor portion 6 can move integrally in the direction B when the accommodating portion 4 moves in the direction B. For example, the accommodating portion 4 may have a configuration in which the pressing mechanism, the rotation driving mechanism and the sensor portion 6 are supported integrally by a flat plate-like member supporting the housing 1.

FIGS. 8A to 8C are views schematically illustrating a portion of the housing 101 shown in FIG. 1, in which the accommodating portion 4 is provided.

Figure 9A:
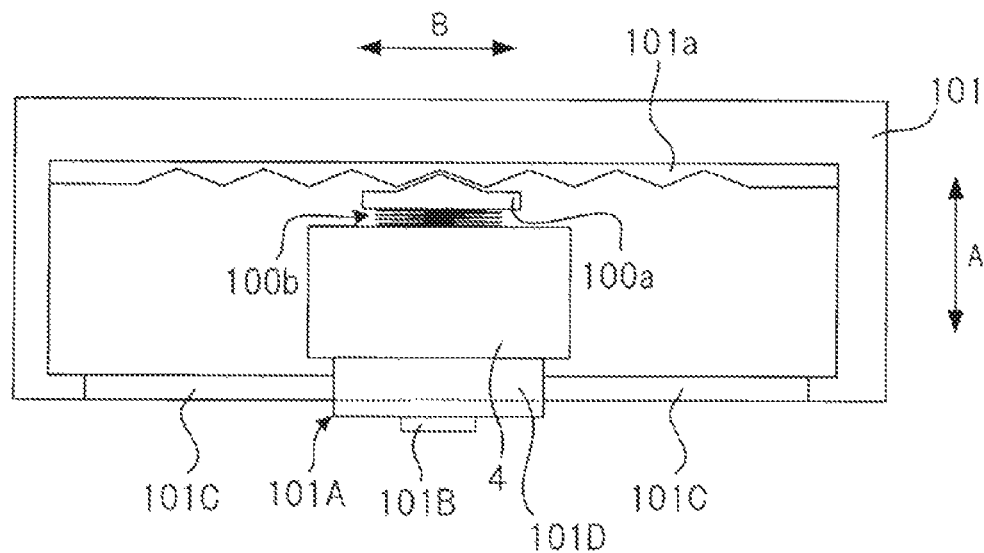
FIGS. 9A and 9B are sectional schematic views taken along a line IX-IX shown in FIG. 8C.
Figure 9B:
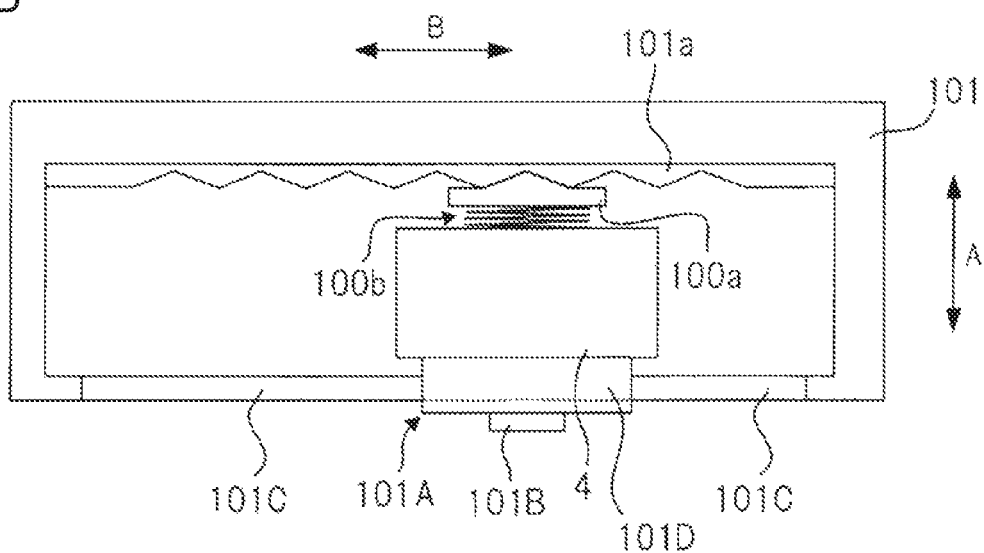

FIG. 8A is a side view of the housing 101 in the state where the biometric information measurement device 200 is attached to the wrist, as seen from a peripheral side (finger side) of the measurement subject. FIG. 8B is a top view of the housing 101 in the state where the biometric information measurement device 200 is attached to the wrist, as seen from the pressing direction. FIG. 8C is a side view of the housing 101 in the state where the biometric information measurement device 200 is attached to the wrist, as seen from a central side (elbow side) of the measurement subject. FIGS. 9A and 9B are sectional schematic views taken along a line IX-IX shown in FIG. 8C.

As shown in FIGS. 8A to 8C, a fixation member 101A fixed to the accommodating portion 4 is provided in, of end surfaces of the housing 101 in the direction A, an end surface (hereinafter referred to as central side end surface) on the central side (elbow side) of the measurement subject in the state where the biometric information measurement device 200 is attached to the wrist. A protrusion 101B is provided on a front surface of the fixation member 101A.

A slit 101C extending in the direction B is formed in the central side end surface of the housing 101. As shown in FIG. 8B, a protrusion 101D penetrating the slit 101C is formed on a back surface of the fixation member 101. The protrusion 101D is fixed to the fixation portion 4. Thus, the fixation member 101A can move in the direction B through the slit 101C.

As shown in FIGS. 9A and 9B, a plate spring 100b is fixed to, of end surfaces of the accommodating portion 4 in the direction A, an end surface on the peripheral side of the measurement subject in the state where the biometric information measurement device 200 is attached to the wrist. A slide member 100a is fixed to the plate spring 100b. The slide member 100a is a member having a triangular prismatic protrusion that is long in the pressing direction (direction perpendicular to the direction A and the direction B).

A slide rail 101a having seven recesses in the example of FIG. 9, with any of which the protrusion of the slide member 100a can be engaged, is formed in the housing 101. The slide member 100a is urged toward the slide rail 101a by the plate spring 100b. Incidentally, a state where a gap is present between the slide member 100a and the slide rail 101a is illustrated in FIG. 9A for the purpose of explanation.

When the measurement subject puts his/her finger on the protrusion 101B in the state shown in FIG. 9A to apply force to the fixation member 101A in a right direction in FIGS. 9, the protrusion of the slide member 100a moves in the right direction along a slope of one of the recesses of the slide rail 101a to engage with an adjacent recess. In this state, the protrusion of the slide member 100a is urged against the recess of the slide rail 101a by the plate spring 100b so as to be brought into a state shown in FIG. 9B.

An interval of adjacent two (distance between bottoms of adjacent two) of the recesses of the slide rail 101a is designed to be, for example, about 1 mm. Thus, with the position shown in FIG. 9A as a reference position, the accommodating portion 4 can be moved 1 mm each time, 3 mm in total, toward one side in the direction B from the reference position, and can be moved 1 mm each time, 3 mm in total, toward the other side in the direction B from the reference position.

Incidentally, 1 mm is an example of the minimum unit for moving the accommodating portion 4. However, the minimum unit is not limited thereto. In addition, the distance over which the accommodating portion 4 can be moved is 6 mm in the above example. However, the numerical value is also exemplified, and the distance is not limited thereto.

Thus, a movement mechanism for moving the accommodating portion 4 in the directions B inside the housing 101 is constituted by the slide rail 101a, the slide member 100a, the plate spring 100b, the fixation member 101A and the protrusion 101B. Incidentally, the mechanism for moving the accommodating portion 4 in the direction B inside the housing 101 is not limited to the one shown in FIGS. 8A to 8C and FIGS. 9A and 9B. A well-known mechanism can be used alternatively.

Figure 10:
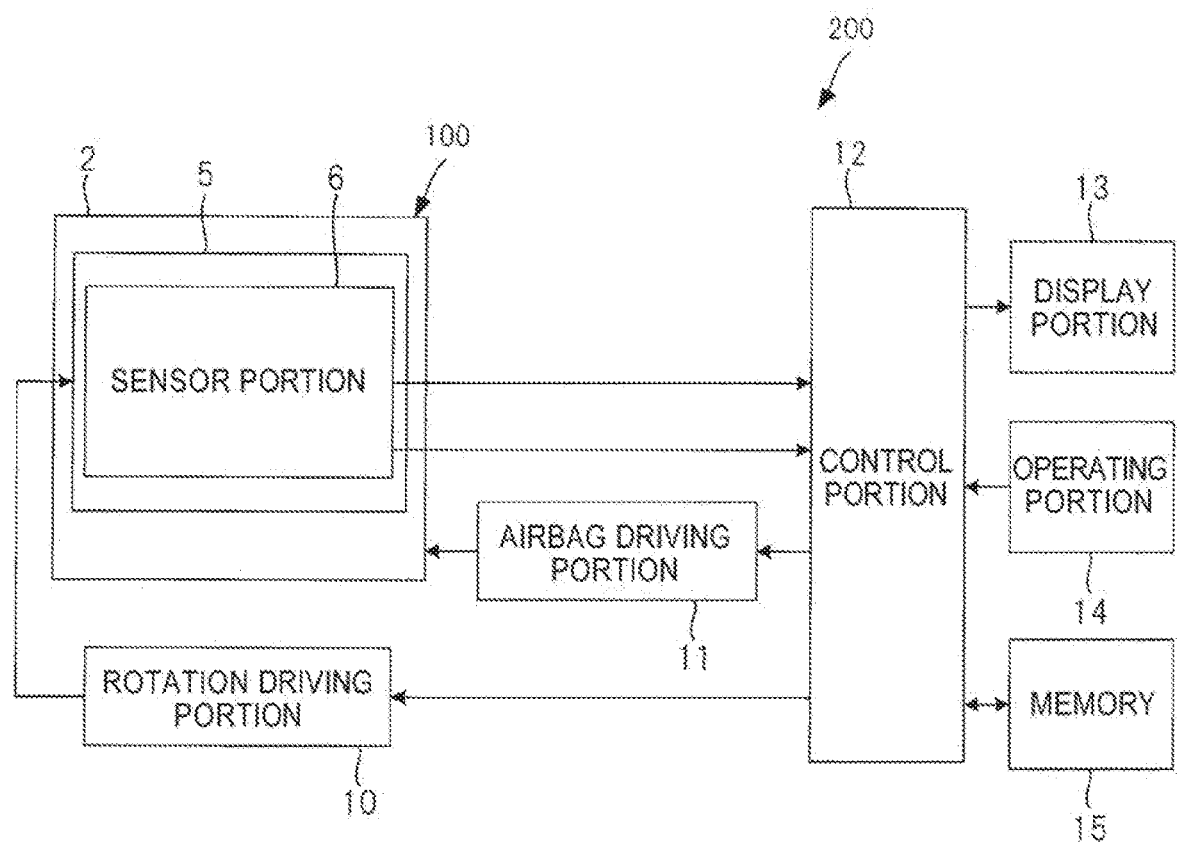
FIG. 10 is a view showing a block configuration of the biometric information measurement device 200 shown in FIG. 1.

FIG. 10 is a view showing a block configuration of the biometric information measurement device 200 shown in FIG. 1.

The biometric information measurement device 200 includes the pressure pulse wave detecting portion 100, the rotation driving portion 10, an air bag driving portion 11, a control portion 12 integrally controlling the device as a whole, the display portion 13, an operating portion 14, and a memory 15.

The rotation driving portion 10 is an actuator that is connected to the rotation axes X and Y of the two-axis rotation mechanism 5a of the pressure pulse wave detecting portion 100. The rotation driving portion 10 drives and rotates each of the rotation axes X and Y in accordance with an instruction of the control portion 12, to rotate the pressing face 6b around the rotation axis X or rotate the pressing face 6b around the rotation axis Y.

The air bag driving portion 11 controls an air volume to be injected into the air bag 2 (internal pressure of the air bag 2) based on the instruction of the control portion 12.

The display portion 13 displays various information such as measured blood pressure values or the like. The display portion 13 is constituted, for example, by a liquid crystal display element, an organic electroluminescent display element, or an electronic paper or the like.

The operating portion 14 is an interface for inputting an instruction signal to the control portion 12. The operating portion 14 is constituted by buttons or the like. for instructing start of various operations including measurement of blood pressure.

The memory 15 includes an ROM (Read Only Memory) storing a program for enabling the control portion 12 to perform predetermined operations and various data, an RAM (Random Access Memory) serving as a work memory, and a flash memory or the like storing various information such as the measured blood pressure data or the like.

The control portion 12 executes the program stored in the ROM of the memory 15 to function as a pressing control portion, a biometric information calculating portion, a rotation control portion, a calibration data creating portion, and a display control portion.

The pressing control portion controls the air bag driving portion 11 to adjust the air volume inside the air bag 2 to control pressing force onto the wrist by the pressing face 6b.

The biometric information calculating portion calculates a first blood pressure value inside the radial artery T based on pressure pulse waves detected by the pressure detecting elements 6a and 7a formed in the pressing face 6b in the state where the pressing face 6b is pressed toward the radial artery T.

Specifically, the biometric information calculating portion calculates the first blood pressure value inside the radial artery T based on the pressure pulse waves detected by the pressure detecting elements 6a and 7a in a process of changing (increasing or decreasing) the pressing force toward the radial artery T by use of the air bag driving portion 11.

The calibration data creating portion creates calibration data using the first blood pressure value calculated by the biometric information calculating portion.

The rotation control portion determines whether rotation of the pressing face 6b by the rotation driving portion 10 is necessary, based on the pressure pulse waves detected by the pressure detecting elements 6a and 7a in the process of increasing the pressing force toward the radial artery T by use of the air bag driving portion 11. When determining that the rotation is required, the rotation control portion controls the rotation driving portion 10 to rotate the pressing face 6b.

The biometric information calculating portion uses the calibration data to calibrate a pressure pulse wave detected for every beat by each of the pressure detecting elements 6a and 7a in the state where the pressing face 6b is pressed toward the radial artery T with most suitable pressing force for deforming a portion of the radial artery T flatly. Thus, the biometric information calculating portion calculates a second blood pressure value inside the radial artery T for every beat.

The display control portion performs display control of the display portion 13.

Operations of the biometric information measurement device 200 according to the present embodiment will be described below. The biometric information measurement device 200 according to the present embodiment has a continuous blood pressure measurement mode of measuring pressure blood values (SBP (Systolic Blood Pressure) that is so-called maximal blood pressure, and DBP (Diastolic Blood Pressure) that is so-called minimal blood pressure) for every heartbeat, storing the measured blood pressure values in the flash memory, and displaying the measured blood pressures on the display portion 13.

Figure 11:
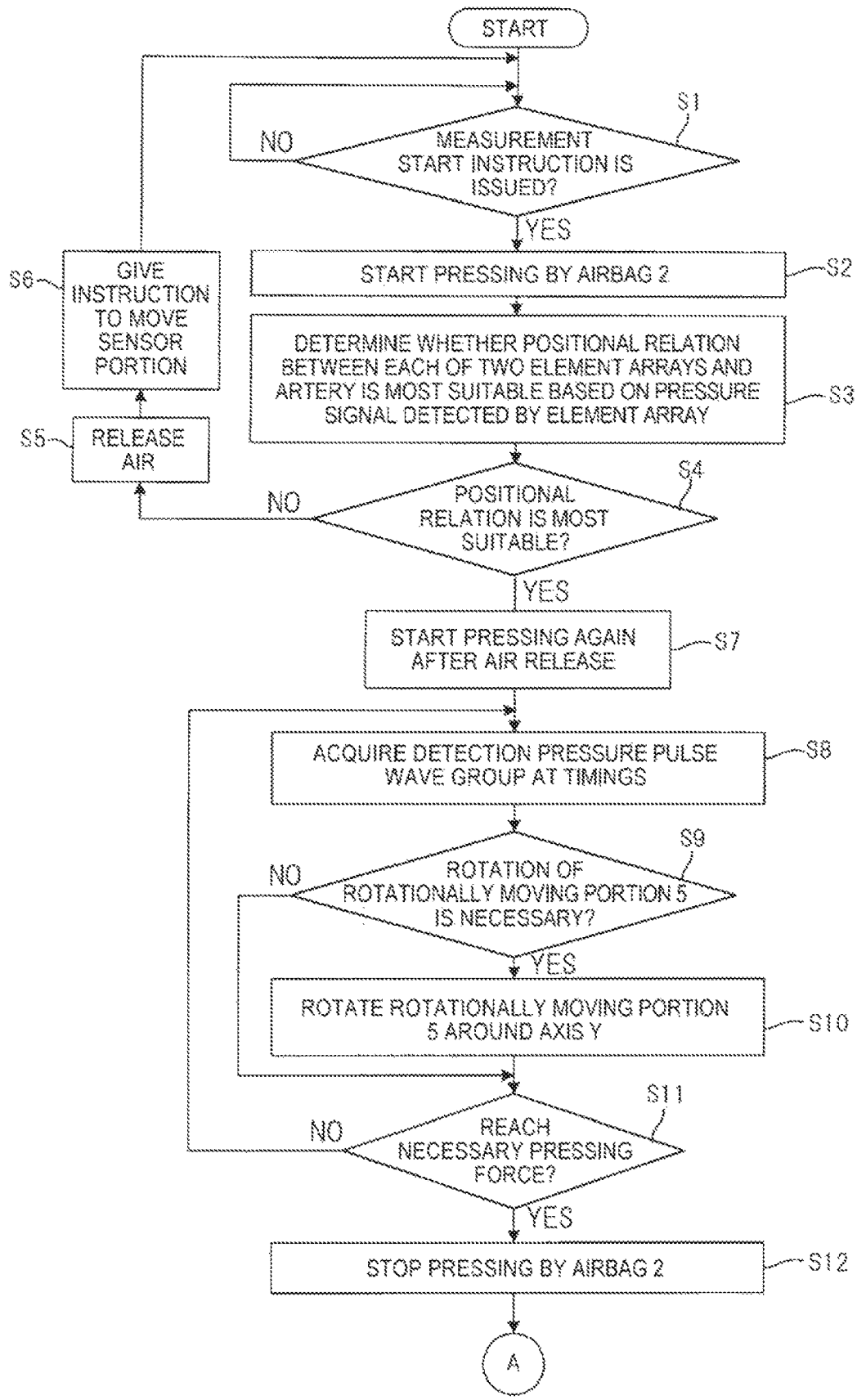
FIG. 11 is a flow chart for explaining operations of the biometric information measurement device 200 shown in FIG. 1 until creation of calibration data.
Figure 12:
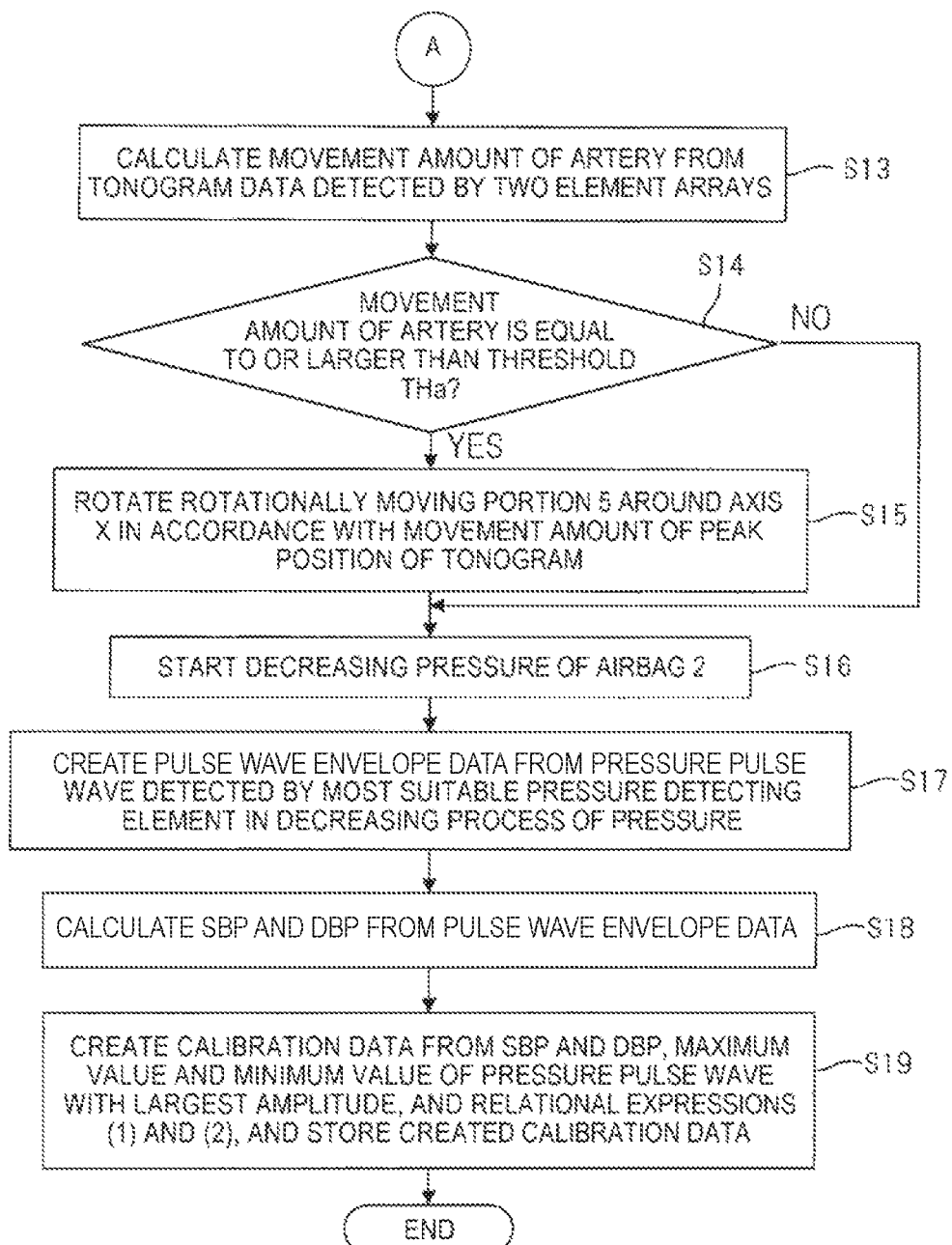
FIG. 12 is a flow chart for explaining the operations of the biometric information measurement device 200 shown in FIG. 1 until the creation of the calibration data.

FIG. 11 and FIG. 12 are flow charts for explaining operations of the biometric information measurement device 200 until creation of calibration data in the continuous blood pressure measurement mode.

Incidentally, the rotationally moving portion 5 of the pressure pulse wave detecting portion 100 has a rotation amount that is set, for example, at zero in an initial state before a blood pressure measurement start instruction is issued so that the pressing face 6b is parallel with the flat plate portion 3.

When a measurement start button included in the operating portion 14 is pushed to issue the blood pressure measurement start instruction (step S1: YES), the control portion 12 controls the air bag driving portion 11 to start injection of air into the air bag 2 to increase pressing force onto the wrist by the pressing face 6b (step S2). When the blood pressure measurement start instruction is not issued, the control portion 12 waits for the blood pressure measurement start instruction.

When time long enough to start occlusion of the radial artery T lapses after the processing of the step S2, the control portion 12 controls the air bag diving portion 11 to stop the injection of the air into the air bag 2. The control portion 12 determines whether the position of the radial artery T with respect to any of the element array 60 and the element array 70 is most suitable, based on a pressure signal detected by each of the element detecting elements 6a of the element array 60 and a pressure signal detected by each of the element detecting elements 7a of the element array 70 in this state (step S3).

"The position of the radial artery T with respect to any of the element arrays is most suitable" means that the radial artery T is present under the vicinity of the center of the element array in the direction B.

For example, assume that the element array has forty-six pressure detecting elements arranged in the direction B. In this case, when the radial artery T is present under twenty-eight pressure detecting elements (pressure detecting elements within a range of the vicinity of the center of the element array) between two ninth pressure detecting elements counted respectively from opposite ends of the forty-six pressure detecting elements, the position of the radial artery T with respect to the element array is regarded as most suitable.

Specifically, the control portion 12 determines the pressure detecting elements each having an amplitude value not smaller than a threshold in an AC component of a pressure signal, as the pressure detecting elements positioned above the radial artery T. The control portion 12 determines that the position of the radial artery T with respect to the element array 60 is most suitable when, of the pressure detecting elements 6a included in the element array 60, all the pressure detecting elements 6a that are determined as positioned above the radial artery T are located within the range of the vicinity of the center set in advance with respect to the element array 60. In a similar manner, the control portion 12 determines that the position of the radial artery T with respect to the element array 70 is most suitable when, of the pressure detecting elements 7a included in the element array 70, all the pressure detecting elements 7a that are determined as positioned above the radial artery T are located within the range of the vicinity of the center set in advance with respect to the element array 70.

When determining that the position of the radial artery T with respect to each of the element array 60 and the element array 70 is not most suitable (step S4: NO), the control portion 12 controls the air bag driving portion 11 to release the air inside the air bag 2 to restore the air bag 2 to the initial state (step S5). The control portion 12 enables the display portion 13 to display information about an instruction to move the accommodating portion 4 in the direction B, and gives the instruction to move the accommodating portion 4 to the measurement subject (step S6). The control portion 12 returns the processing to the step S1 after the step S6.

For example, a message "The artery cannot be detected accurately. Please push the measurement start button again after moving the sensor unit." is displayed on the display portion 13 by the processing of the step S6. The measurement subject who sees the display is instructed to move the protrusion 101B and the fixation member 101A shown in FIG. 8C a minimum unit (1 mm in the above example) to the left or right.

When the measurement subject then pushes the measurement start button so that the determination of the step S1 is YES, the processing of the steps S2 to S4 is performed again. When determining that the position of the radial artery T with respect to any of the element array 60 and the element array 70 is most suitable in the step S4 (step S4: YES), the control portion 12 controls the air bag driving portion 11 to release the air inside the air bag 2, and then starts injection of air into the air bag 2 again to increase pressing force onto the wrist by the pressing face 6b (step S7).

In the increasing process of the pressing force started in the step S7, the control portion 12 acquires a plurality of pieces of pressure pulse wave information I1 in order from a latest detection time instant, of a group of pressure pulse waves (referred to as pieces of pressure pulse wave information I1) that are detected by the pressure detecting elements 6a so far and stored in the memory 15 at arbitral timings (e.g. periodical timings) after a lapse of time long enough to start the occlusion of the radial artery T. In addition, the control portion 12 acquires, of a group of pressure pulse waves (referred to as pieces of pressure pulse wave information I2) that are detected by the pressure detecting elements 7a so far and stored in the memory 15 at the above arbitral timings, a plurality of pieces of pressure pulse wave information I2 in order from the latest detection time instant (step S8).

Of the plurality of pieces of pressure pulse wave information I1 acquired in the step S8, the control portion 12 calculates, for example, an average value Ave1 of amplitudes of pressure pulse waves included in pieces of pressure pulse wave information I1 detected at a time instant t1, and calculates an average value Ave2 of amplitudes of pressure pulse waves included in pieces of pressure pulse wave information I1 detected at a time instant t2 later than the time instant t1. In addition, of the pieces of pressure pulse wave information I2 acquired in the step S8, the control portion 12 calculates an average value Ave3 of amplitudes of pressure pulse waves included in pieces of pressure pulse wave information I2 detected at the time instant t1, and calculates an average value Ave4 of amplitudes of pressure pulse waves included in pieces of pressure pulse wave information I2 detected at the time instant t2. The control portion 12 calculates ratios ((Ave1/Ave3) and (Ave2/Ave4)) of the average values calculated with respect to the same time instants.

The control portion 12 determines whether the rotationally moving portion 5 should be rotated by the rotation driving portion 10, based on a change in the ratios calculated as to a plurality of timings. That is, the control portion 12 determines whether to rotate the rotationally moving portion 5, based on the pressure pulse waves detected by the pressure detecting elements 6a and 7a at the plurality of timings in the increasing process of the pressing force (step S9).

When, for example, the ratios calculated as to the plurality of timings increase monotonically, determination can be made that the element array 70 moves in a direction to occlude the radial artery T but the element array 60 does not move in the direction to occlude the radial artery T. Therefore, the control portion 12 determines that rotation of the rotationally moving portion 5 is necessary.

In addition, when the ratios calculated as to the plurality of timings decrease monotonically, determination can be made that the element array 60 moves in the direction to occlude the radial artery T but the element array 70 does not move in the direction to occlude the radial artery T. Therefore, the control portion 12 determines that rotation of the rotationally moving portion 5 is necessary.

In addition, when the ratios calculated as to the plurality of timings almost do not change, determination can be made that the element arrays 60 and 70 equally detect pressure pulse waves accurately from the radial artery T. Therefore, the control portion 12 determines that rotation of the rotationally moving portion 5 is not necessary.

In addition, when the ratios calculated as to the plurality of timings increase/decrease repeatedly, it is not possible to determine whether the element arrays 60 and 70 pass the radial artery T sufficiently or only one of the element arrays 60 and 70 presses the radial artery T sufficiently. Therefore, the control portion 12 determines that rotation of the rotationally moving portion 5 is not necessary.

Thus, the control portion 12 determines whether the rotation is necessary, based on a change in the ratios calculated as to the plurality of timings. Incidentally, a difference (having a value considering a sign) between the average value Ave1 (Ave2) and the average value Ave3 (Ave4) may be used in place of the ratio.

Figure 13A:
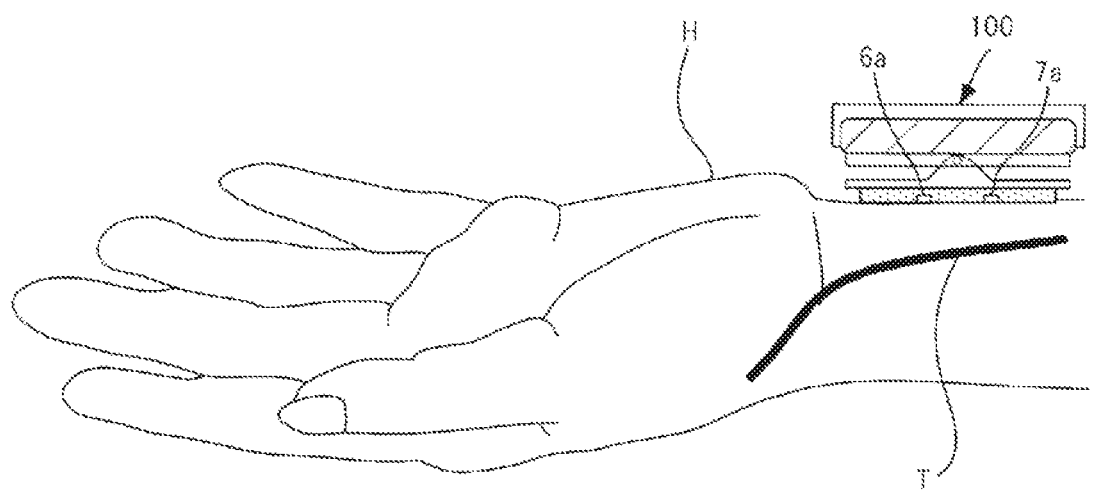
FIGS. 13A and 13B are views each illustrating an example of a state where one of two element arrays is not occluded a radial artery in the biometric information measurement device 200 shown in FIG. 1.

FIG. 13A is a view showing an example of a state where the radial artery T is occluded by the element array 70 but the radial artery T is not occluded by the element array 60. In the state of FIG. 13A, a distance between the element array 60 and the radial artery T is larger than a distance between the element array 70 and the radial artery T.

Figure 13B:
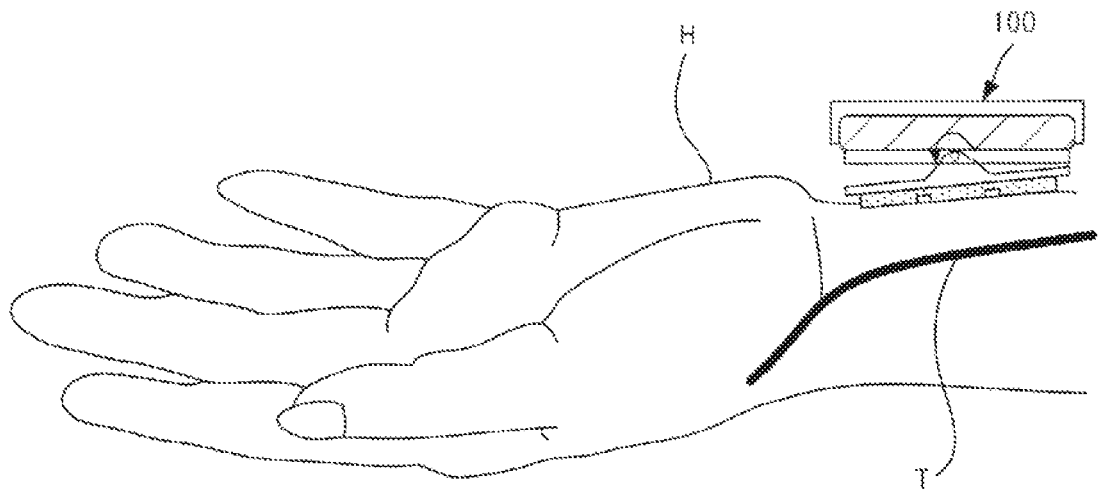

When the average value of the amplitudes of the pressure pulse waves detected respectively by the pressure detecting elements 6a is designated as 6A and the average value of the amplitudes of the pressure pulse waves detected respectively by the pressure detecting elements 7a is designated as 7A, a ratio (6A/7A) of 6A to 7A is larger than "1" in the state of FIGS. 13A and 13B. When the element array 60 is made closer to the radial artery T in this state, (6A/7A) is closer to 1.

Therefore, when determining that rotation of the rotationally moving portion 5 around the rotation axis Y is necessary in the step S9, the control portion 12 performs rotation control of the rotationally moving portion 5 around the rotation axis Y in accordance with the value (6A/7A) at a latest time instant (step S10).

Specifically, the control portion 12 reads a rotation amount corresponding to the value (6A/7A) with reference to a data table (which is obtained experimentally prior to product shipment and stored in the memory 15 in advance) showing the relation between the value (6A/7A) and the rotation amount of the rotationally moving portion 5, and sets the read rotation amount.

In addition, the control portion 12 determines which is larger, the average value 6A or the average value 7A. When the average value 6A is larger, the control portion 12 sets the rotation direction of the rotationally moving portion 5 around the rotation axis Y as counterclockwise in FIGS. 13A and 13B in order to reduce the distance between the element array 60 and the radial artery T.

When the average value 7A is larger, the control portion 12 sets the rotation direction of the rotationally moving portion 5 around the rotation axis Y as clockwise in FIGS. 13A and 13B in order to reduce the distance between the element array 70 and the radial artery T.

The control portion 12 rotates the rotationally moving portion 5 in accordance with the rotation direction and the rotation amount set thus. Thus, the pressing face 6b and the radial artery T can be made parallel with each other so as to obtain a state where the radial artery T is pressed uniformly over a wide range, as shown in FIG. 13B.

After the step S10 or when rotation of the rotationally moving portion 5 is determined as not necessary in the step S9, the control portion 12 shifts the processing to a step S11. In the step S11, the control portion 12 determines whether the pressing force reaches pressure (necessary pressing force) enough to occlude the radial artery T. When the pressing force reaches the necessary pressing force (step S11: YES), the control portion 12 controls the air bag driving portion 11 to stop the injection of the air into the air bag 2 (step S12). When the pressing force does not reach the necessary pressing force, the control portion 12 returns the processing to the step S8.

After the step S12, the control portion 12 obtains an amplitude distribution curve, that is a so-called tonogram, showing the relation between the amplitudes of the pressure pulse waves detected respectively by the pressure detecting elements 6a at the same time instant in the steps S7 to S12, and the positions of the pressure detecting elements 6a on the pressing face 6b. In addition, the control portion 12 obtains another tonogram showing the relation between the amplitudes of the pressure pulse waves detected respectively by the pressure detecting element 7a at the same time instant, and the positions of the pressure detecting elements 7a on the pressing face 6b.

The control portion 12 stores the tonogram created for the element array 60 into the memory 15 in association with identification information of the element array 60, the detection time instant of the pressure pulse waves, the pressing force (internal pressure of the air bag 2) in the pressing direction by the air bag 2 at the detection time instant.

In a similar manner, the control portion 12 stores the tonogram created for the element array 70 into the memory 15 in association with identification information of the element array 70, the detection time instant of the pressure pulse waves, the pressing force in the pressing direction by the air bag 2 at the detection time instant.

The control portion 12 uses the data of the tonograms stored in the memory 15 to calculate a movement amount of the radial artery T in the direction B during the pressing of the pressing face 6b onto the wrist (step S13).

Figure 14A:
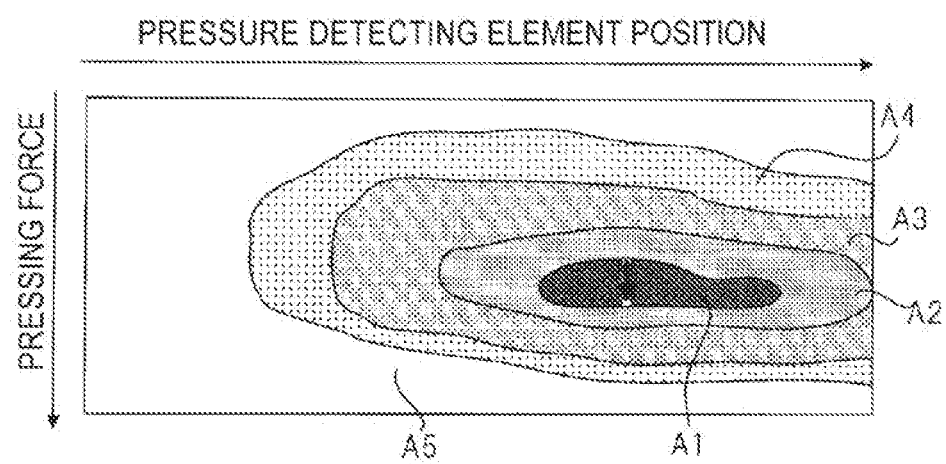
FIGS. 14A and 14B are views each illustrating an example of an amplitude value of a pressure pulse wave detected by each pressure detecting element of a sensor portion 6 when pressing force on the wrist by the sensor portion 6 of the biometric information measurement device 200 shown in FIG. 1 is changed.
Figure 14B:
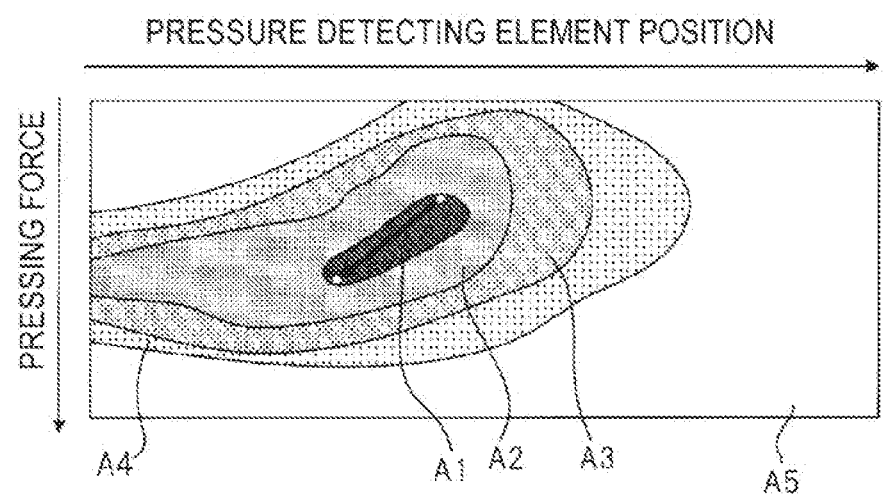

FIGS. 14A and 14B are graphs showing examples of the amplitude values of the pressure pulse waves detected by the pressure detecting elements 6a of the sensor portion 6 when the pressing force applied to the wrist by the sensor portion 6 is changed. In FIGS. 14A and 14B, the abscissa expresses the position of each of the pressure detecting elements 6a in the direction B, and the ordinate expresses the pressing force.

In FIGS. 14A and 14B, the amplitudes of the pressure pulse waves detected by the pressure detecting elements 6a at the positions are colored based on the magnitudes of the amplitudes.

A sign A1 designates a portion in which the amplitude is not smaller than a threshold TH1. A sign A2 designates a portion in which the amplitude is not smaller than a threshold TH2 but smaller than the threshold TH1. A sign A3 designates a portion in which the amplitude is not smaller than a threshold TH3 but smaller than the threshold TH2. A sign A4 designates a portion in which the amplitude is not smaller than a threshold TH4 but smaller than the threshold TH3. A sign A5 designates a portion in which the amplitude is smaller than the threshold TH4. That is, threshold TH1>threshold TH2>threshold TH3>threshold TH4.

FIG. 14A shows an example in which a pressure detecting element 6a detecting a pressure pulse wave with an amplitude not smaller than the threshold TH1 has an almost fixed position in the increasing process of the pressing force. On the other hand, FIG. 14B shows an example in which a pressure detecting element 6a detecting a pressure pulse wave with an amplitude not smaller than the threshold TH1 has a position gradually deviated leftward in the increasing process of the pressing force.

Figure 15A:
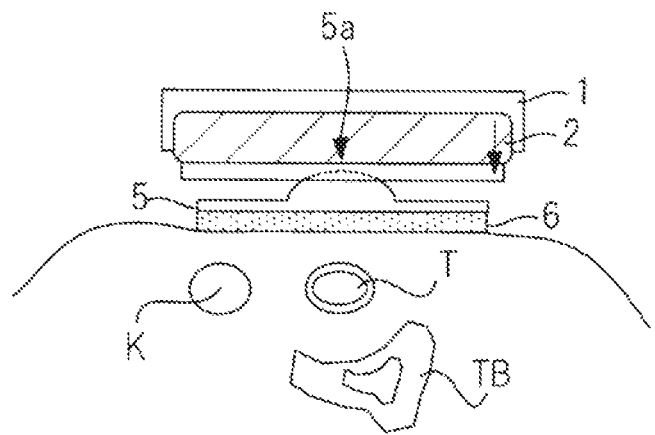
FIGS. 15A to 15C are views illustrating a state where the pressure pulse wave detecting portion 100 of the biometric information measurement device 200 shown in FIG. 1 is contacted to the wrist and the sensor portion 6 is pressed onto the wrist by an air bag 2.
Figure 15B:
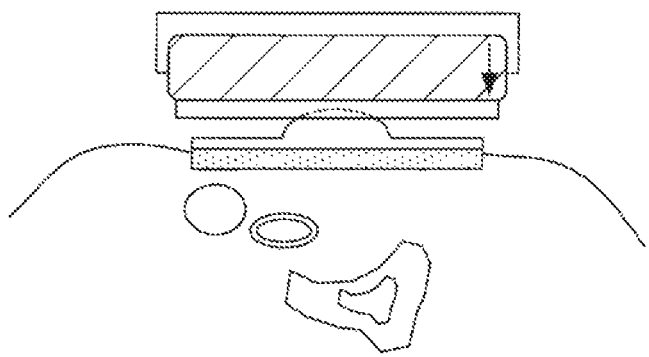
Figure 15C:
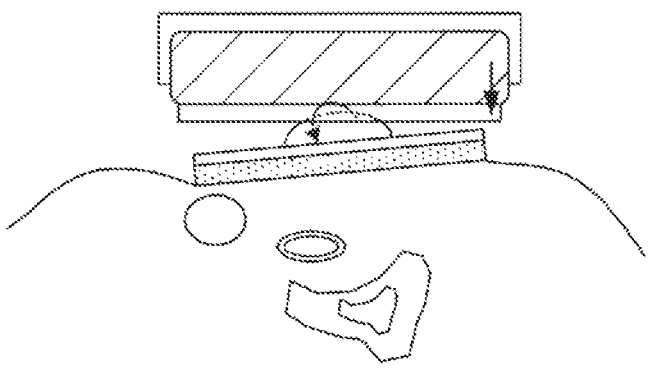

FIGS. 15A to 15C are views each showing a state where the pressure pulse wave detecting portion 100 is put on a wrist to press the sensor portion 6 onto the wrist by the air bag 2. In FIGS. 15A to 15C, the sign TB designates a radius, and the sign K designates a tendon.

When the sensor portion 6 is pressed onto the wrist as shown in FIG. 15A, a radial artery T may move in the direction B as shown in FIG. 15B.

When the radial artery T moves in the direction B during the pressing as shown in FIG. 15B, amplitude values of pressure pulse waves during the pressing has a distribution as shown in FIG. 14B. That is, there occurs a large deviation between the position of a pressure detecting element 6a that detected an amplitude value not smaller than the threshold TH1 in pressing force with which the amplitude value was detected for the first time, and the position of a pressure detecting element 6a that detected an amplitude value not smaller than the threshold TH1 in pressing force with which the amplitude value was detected for the last time.

In the example of FIG. 14A, there occurs no large deviation between the position of a pressure detecting element 6a that detected an amplitude value not smaller than the threshold TH1 in pressing force with which the amplitude value was detected for the first time, and the position of a pressure detecting element 6a that detected an amplitude value not smaller than the threshold TH1 in pressing force with which the amplitude value was detected for the last time. That is, it can be known that the radial artery T can be occluded substantially without moving in the direction B in the increasing process of the pressing force.

Thus, when the change of the tonogram in the changing process of the pressing force is viewed, the change of the position as to the radial artery T in the direction B can be detected. When the pressing force is increased to occlude the radial artery T while the state shown in FIG. 15B is kept as it is, there is a possibility that an accurate tonogram cannot be obtained due to the influence of biological tissues such as the tendon K.

Therefore, from the data of FIGS. 14A and 14B each showing the relation between the pressing force and the tonogram, the control portion 12 calculates a difference (i.e. a movement amount of the radial artery T in the direction B) between the position of the pressure detecting element 6a that detected the amplitude value not smaller than the threshold TH1 in the pressing force with which the amplitude value was detected for the first time, and the position of the pressure detecting element 6a that detected the amplitude value not smaller than the threshold TH1 in the pressing force with which the amplitude value was detected for the last time in the step S13, and determines whether the calculated difference is equal to or larger than a threshold THa (step S14).

Incidentally, the control portion 12 may calculate the movement amount of the radial artery T in the direction B based on the data showing the relation between the tonogram created for the element array 70 and the pressing force, and compare the calculated movement amount with the threshold THa.

When the above movement amount is equal to or larger than the threshold THa (step S14: YES), the control portion 12 obtains a vector indicated by an arrow of FIG. 14B in a step S15. When the difference between the two positions is smaller than the threshold THa (step S14: NO), processing of a step S16 is performed.

The direction and the magnitude of the vector shown in each of FIGS. 14A and 14B and information showing how much and in which direction the rotationally moving portion 5 should be rotated around the rotation axis X are experimentally obtained in advance and stored in advance in the memory 15 in association with each other.

The control portion 12 acquires information about a rotation direction and a rotation amount corresponding to the magnitude and the direction of the obtained vector from the memory 15, and transmits the acquired information to the rotation driving portion 10. The rotation driving portion 10 rotates the rotationally moving portion 5 as shown in FIG. 15C in accordance with the received information (step S15).

In the step S16 following the step S15, the control portion 12 controls the air bag driving portion 11 to release the air inside the air bag 2 to start decrease of the pressing force toward the radial artery T.

After starting the decrease of the pressing force in the step S16 to decrease the pressing force to a minimum value, the control portion 12 determines a most suitable pressure detecting element from all the pressure detecting elements 6a, 7a. The control portion 12 determines, for example, a pressure detecting element that detects a pressure pulse wave with the largest amplitude in a decreasing process of the pressing force, as the most suitable pressure detecting element.

The pressure pulse wave detected by the pressure detecting element positioned right above a portion where the radial artery T is made flat has the largest amplitude without being affected by tension of the wall of the radial artery T. The pressure pulse wave has highest correlation with blood pressure values inside the radial artery T. For such a reason, the pressure detecting element that detects the pressure pulse wave with the largest amplitude is determined as the most suitable pressure detecting element.

Incidentally, in some case, there may be a plurality of pressure detecting elements that detect the pressure pulse waves with the largest amplitude respectively. In this case, the plurality of pressure detecting elements are treated as the most suitable pressure detecting element. For example, an average of the pressure pulse waves detected respectively by the plurality of pressure detecting elements may be treated as the pressure pulse wave detected by the most suitable pressure detecting element.

The control portion 12 creates pulse wave envelope data from the pressure pulse wave detected by the most suitable pressure detecting element in the decreasing process of the pressing force (step S17).

The pulse wave envelope data are data in which the pressing force (internal pressure of the air bag 2) toward the radial artery T by the sensor portion 6 and the amplitude of the pressure pulse wave detected by the most suitable pressure detecting element in the state where the most suitable pressure detecting element is pressed toward the radial artery T with the pressing force are associated with each other.

FIG. 16 is a view showing a change of the pressing force toward the radial artery T, and a change of pressure pulse waves detected by the most suitable pressure detecting element by way of example. In FIG. 16, a straight line designated as a sign P expresses the pressing force, and a waveform designated as a sign M expresses the pressure pulse waves. An enlarged view of one of the pressure pulse waves is shown in a lower part of FIG. 16.

As shown in FIG. 16, in the pressure pulse wave, pressure at a rising point is a minimum value Mmin, and pressure at a falling point is a maximum value Mmax. The amplitude of the pressure pulse wave is a value obtained by subtracting the minimum value Mmin from the maximum value Mmax. Each of the maximum value Mmax and the minimum value Mmin is a piece of information for identifying the shape of the pressure pulse wave.

As shown in FIG. 16, when the pressing force starts decreasing to remove the occluded state of the radial artery T, the amplitude of the pressure pulse wave detected by the most suitable pressure detecting element increases suddenly and then changes as illustrated in FIG. 16 in accordance with the decrease of the pressing force. In the step S17, the control portion 12 creates the pulse wave envelope data shown in FIG. 17 from the relation between the pressing force and the pressure pulse wave shown in FIG. 16.

Figure 17:
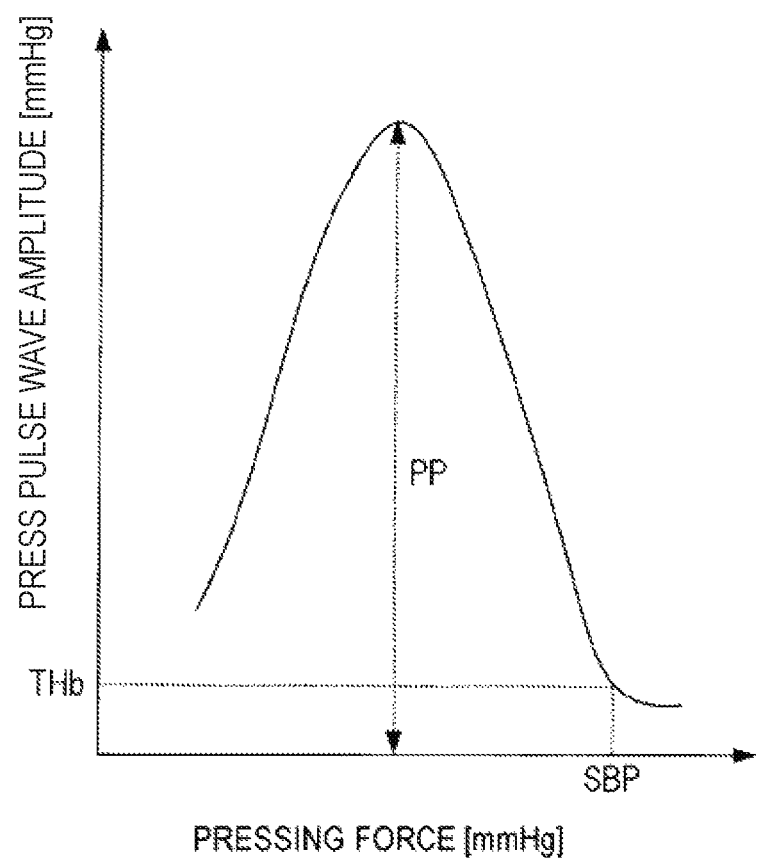
FIG. 17 shows a graph showing an example of pulse wave envelope data.

When the pulse wave envelope data shown in FIG. 17 are created, the control portion 12 calculates SBP and DBP from the created pulse wave envelope data (step S18).

For example, the control portion 12 determines, as the SBP, the pressing force at a time point at which the amplitude of the pressure pulse wave starts increasing suddenly after the pressing force starts decreasing in the pulse wave envelope shown in FIG. 17, i.e. the pressing force at a time point at which the amplitude of the pressure pulse wave detected by the most suitable pressure detecting element exceeds a threshold THb for the first time after the pressing force starts decreasing. The threshold THb is a value by which the artery can be determined to be no longer occluded when the pressing force exceeds the value. Alternatively, the control portion 12 calculates a difference between adjacent two amplitude values in the pulse wave envelope data, and determines, as the SBP, the pressing force at a time point at which the difference exceeds a threshold.

Further, the control portion 12 sets the largest value of the amplitude of the pressure pulse wave as pulse pressure (PP) in the pulse wave envelope shown in FIG. 17, and calculates DBP from the obtained SPB and PP and in accordance with a relational expression SBP−DBP=PP.

After the step S18, the control portion 12 creates calibration data using the maximum value Mmax and the minimum value Mmin of any (e.g. a pressure pulse wave whose amplitude is the largest) of the pressure pulse waves detected by the most suitable pressure detecting element determined in the decreasing pressure process in and after the step S16 and the SBP and the DBP calculated in the step S18, and stores the created calibration data into the memory 15 (step S19). The calibration data are used when continuous blood pressure measurement which will be described later is performed.

When a designates a slope of a linear function and b designates an intercept of the linear function, the following relations are satisfied.

$$SBP = a \times M\text{max} + b \quad (1)$$

$$DBP = a \times M\text{min} + b \quad (2)$$

The control portion 12 substitutes the SBP and the DBP obtained in the step S18 and the maximum value Mmax and the minimum value Mmin of the pressure pulse wave whose amplitude is the largest in the pulse wave envelope of FIG. 17, in the expression (1) and the expression (2) so as to calculate the slope a and the intercept b. The calculated coefficients a and b and the expressions (1) and (2) are stored as the calibration data in the memory 15.

Figure 18:
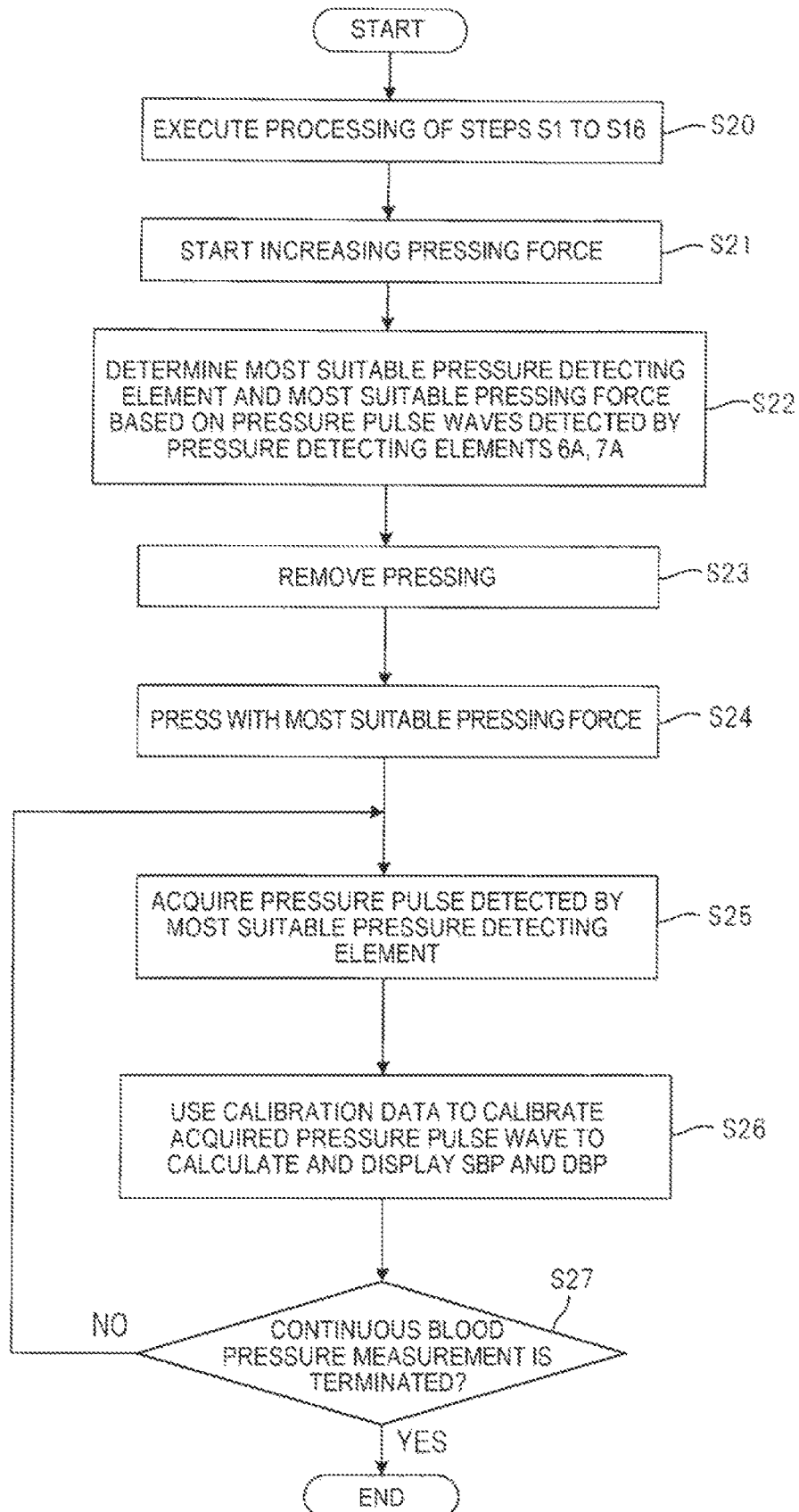
FIG. 18 is a flow chart for explaining continuous blood pressure measurement operations in a continuous blood pressure measurement mode of the biometric information measurement device 200 shown in FIG. 1.

FIG. 18 is a flow chart for explaining continuous blood pressure measurement operations of the biometric information measurement device 200 according to the present embodiment in the continuous blood pressure measurement mode.

When the continuous blood pressure measurement mode is set and a blood pressure measurement start instruction is issued, first, the same processing as that in the steps S1 to S16 shown in FIGS. 11 and 12 is performed (step S20). When pressing force then reaches a minimum value, the control portion 12 controls the air bag driving portion 11 to increase internal pressure of the air bag 2 to increase the pressing force onto the wrist by the pressing face 6b (step S21).

Next, the control portion 12 determines, of the pressure detecting elements 6a, 7a, a pressure detecting element that detects a pressure pulse wave with the largest amplitude in an increasing process of the pressing force, as a most suitable pressure detecting element. In addition, the control portion 12 determines the internal pressure of the air bag 2 at a time point at which the pressure pulse wave with the largest amplitude is detected, as most suitable pressing force (step S22).

Next, the control portion 12 removes the internal pressure of the air bag 2 to restore the air bag 2 to an initial state (step S23). Then, the control portion 12 increases the internal pressure of the air bag 2 to the most suitable pressing force determined in the step S22, and maintains the most suitable pressing force (step S24).

Next, the control portion 12 acquires a pressure pulse wave detected by the most suitable pressure detecting element determined in the step S22 in the state where the pressing face 6b is pressed onto the wrist with the most suitable pressing force (step S25).

The control portion 12 uses the calibration data created in the step S19 of FIG. 12 to calibrate the acquired pressure pulse wave, calculates SBP and DBP which are second blood pressure values, and displays the calculated SBP and the calculated DBP on the display portion 13 (step S26).

Specifically, the control portion 12 substitutes a maximum value Mmax of the pressure pulse wave acquired in the step S25, and the coefficients a and b calculated in the step S19 in the above expression (1) so as to calculate the SBP. The control portion 12 substitutes a minimum value Mmin of the pressure pulse wave acquired in the step S25, and the coefficients a and b calculated in the step S19 for in above expression (2) so as to calculate the DBP. When a continuous blood pressure measurement termination instruction is issued (step S27: YES), the control portion 12 terminates the processing. When the termination instruction is not issued (step S27: NO), the control portion 12 returns the processing to the step S25.

According to the biometric information measurement device 200 as described above, the pressing face 6b is configured to be rotatable around each of the rotation axis X and the rotation axis Y. Accordingly, the contact state between the sensor portion 6 and the living body part can be changed flexibly so that pressure pulse wave detection accuracy can be improved.

In addition, according to the biometric information measurement device 200, the processing in and after the step S7 of FIG. 11 can be performed in a state where the position of the radial artery T with respect to the element array 60 or the element array 70 is most suitable. Therefore, the processing in and after the step S8 can be performed in a state where pressure pulse waves can be detected from the radial artery T by many of pressure detecting elements. Processing of determination as to whether rotation is necessary in the step S9 of FIG. 11, processing of rotation control of the rotationally moving portion 5 around the rotation axis Y in the step S10 of FIG. 11, processing of calculation of a movement amount of the artery in the step S13 of FIG. 12, and processing of rotation control of the rotationally moving portion 5 around the rotation axis X in the step S15 of FIG. 12 can be performed with high accuracy. As a result, accurate calibration data and blood pressure information can be calculated.

In addition, according to the biometric information measurement device 200, the fixation member 101A is disposed in the end surface of the housing 101 on the central side of the measurement subject in the state where the biometric information measurement device 200 is attached to the wrist. Therefore, while holding the opposite end surfaces of the housing 101 in the direction A with a right hand on which the biometric information measurement device 200 is not attached, the measurement subject can use the thumb of the right hand to easily apply force to the fixation member 101A. Thus, operability for moving the accommodating portion 4 is improved.

Incidentally, configuration may be made alternatively so that the slit 101C shown in FIG. 8C is formed in an upper surface (surface shown in FIG. 8B) of the housing 101, and the fixation member penetrating the slit 101C and fixed to the accommodating portion 4 is provided in the upper surface. According to the configuration, the fixation member is easily visually recognized so that operability for moving the accommodating portion 4 is improved.

Incidentally, the biometric information measurement device 200 calculates blood pressure information including SBP and DBP based on pressure pulse waves detected by the pressure detecting elements of the sensor portion 6. However, the biometric information measurement device 200 may calculate and store biometric information such as a pulse rate or a heart rate in place of the blood pressure information.

In addition, the movement mechanism for moving the accommodating portion 4 is a mechanism moving the accommodating portion 4 in the direction B by a manual operation for manually moving the fixation member 101A (mechanism moving the accommodating portion 4 without using any driving source). However, the movement mechanism is not limited thereto.

For example, configuration may be made alternatively so that an actuator for driving the accommodating portion 4 is added inside the housing 101 and the control portion 12 moves the accommodating portion 4 in the direction B through the actuator. According to the configuration in which the accommodating portion 4 is moved manually, the mechanism of the biometric information measurement device 200 can be simplified so that manufacturing cost of the biometric information measurement device 200 can be reduced.

The pressure pulse wave detecting portion 100 has a configuration in which the element array 60 and the element array 70 are formed in one pressing face. However, the pressure pulse wave detecting portion 100 may alternatively have a configuration in which an element array is formed in each of divided faces into which the pressing face is divided.

According to the configuration in which the pressing face is divided, the degree of freedom for design of the pressure pulse wave detecting portion 100 is improved. Therefore, structure design or the like for making the contact state of the pressing face with the skin excellent can be so easy that an improvement in attachability or the like can be expected.

On the other hand, in the configuration of FIG. 7, pressing force can be easily transmitted to the artery uniformly so that an improvement in pressure pulse wave measurement accuracy can be expected.

In the example of FIG. 7, the rotation axis Y is set between the element array 60 and the element array 70. However, setting of the rotation axis Y is not limited thereto. For example, the rotation axis Y may be set outside the element array 60 and the element array 70.

Specifically, the rotation axis Y may be provided on a left side of the element array 60 in FIG. 7. Alternatively, the rotation axis Y may be provided on a right side of the element array 70 in FIG. 7.

In a similar manner, the rotation axis X is disposed at a position dividing each of the two element arrays into halves in the example of FIG. 7. Disposition of the rotation axis X is however not limited thereto. For example, the rotation axis X may be disposed at any position on each of the element arrays. In addition, the rotation axis X may be set at a position not intersecting with each of the element arrays (on an upper side or a lower side of the sensor portion 6).

In the above description, two element arrays are formed in the pressing face 6b. However, three or more element arrays may be formed in the pressing face 6b alternatively. When the three or more element arrays are used, whether rotation of the pressing face 6b around each of the rotation axis X and the rotation axis Y is necessary and the rotation amount can be determined with higher accuracy so that biometric information can be calculated with higher accuracy.

The determination method as to whether rotation of the pressing face 6b around each of the rotation axis X and the rotation axis Y is necessary as described in FIGS. 11 and 12, and the determination method of the rotation amount and the rotation direction for rotating the pressing face 6b are exemplified. However, other methods than the above methods may be used alternatively.

The movement mechanism shown in FIGS. 8A to 8C and 9A and 9B has a configuration in which the fixation member 101A is slid in the direction B to move the accommodating portion 4 in the direction B.

A mechanism in which a rotatable member is provided on an outer circumference surface of the housing 101, and the member is rotated to move the accommodating portion 4 in the direction B may be used as a modification of the movement mechanism.

Figure 19:
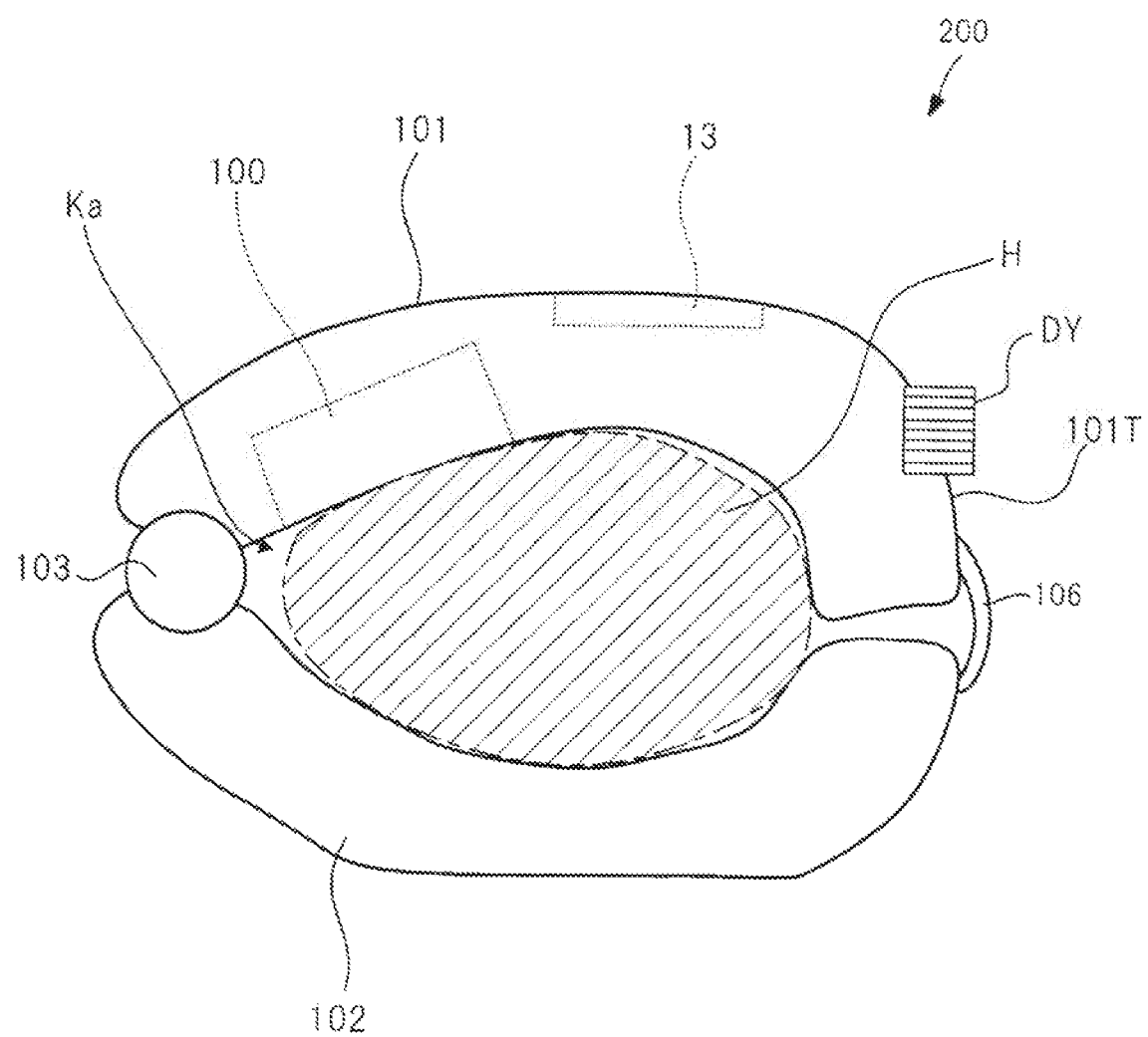
FIG. 19 is a view showing a modification of the biometric information measurement device 200 shown in FIG. 1.

For example, as shown in FIG. 19, a dial DY rotatable around the direction B serving as a rotation axis is provided on, of end surfaces of the housing 101 in the direction B, an ulnar-side end surface 101T (end surface closer to an opposite hand to the hand of the measurement subject on which the biometric information measurement device 200 is attached). When the dial DY is rotated, the accommodating portion 4 moves in the direction B in accordance with the rotation amount.

When the accommodating portion 4 is moved by the dial operation, operability can be improved. In addition, with provision of the dial DY on the end surface 101T where the dial DY is easily operated by the right hand opposite to the hand of the measurement subject on which the biometric information measurement device is attached, as in the configuration shown in FIG. 19, operability can be improved.

The above-disclosed embodiment should be considered in all respects to be illustrative and not restrictive. The scope of the present invention is represented by the appended claims rather than the foregoing description, and all changes within the meaning and range of equivalents thereof are intended to be covered therein.

As described above, the following matters are disclosed in the specification.

The disclosed pressure pulse wave detector includes: a pressing member which includes a pressing face in which element arrays each including pressure detecting elements arranged in one direction are arranged in a direction intersecting with the one direction; a pressing mechanism which is configured to press the pressing face against a body surface of a living body in a state where the one direction intersects with an extension direction of an artery under the body surface; a rotation driving mechanism which is configured to rotate the pressing face around each of two axes which are perpendicular to a pressing direction of the pressing face pressed by the pressing mechanism and include a first axis extending in the one direction and a second axis perpendicular to the one direction; a support member which supports the pressing mechanism, the rotation driving mechanism and the pressing member; a housing which houses therein the support member; and a movement mechanism which is configured to move the support member in the one direction inside the housing.

In the disclosed pressure pulse wave detector, the movement mechanism is configured to move the support member in the one direction by a manual operation.

In the disclosed pressure pulse wave detector, the pressure pulse wave detector is used while the housing is attached to a wrist of a measurement subject, the movement mechanism includes a fixation member which is fixed to the support member, and the fixation member is provided to be movable in the one direction on an end surface on a central side of the measurement subject in a state where the housing is attached to the wrist, among end surfaces of the housing in a direction perpendicular to the one direction and the pressing direction.

In the disclosed pressure pulse wave detector, the movement mechanism includes a rotatable member and is configured to move the support member in the one direction in accordance with rotation of the rotatable member.

In the disclosed pressure pulse wave detector, the pressure pulse wave detector is used while the housing is attached to a wrist of a measurement subject, and the rotatable member is rotatable around the one direction as a rotation axis and is provided on an end surface close to a hand other than a hand on which the housing is attached, among end surfaces of the housing in the one direction.

The disclosed biometric information measurement device includes: the above pressure pulse wave detector; and a biometric information calculating portion which is configured to calculate biometric information based on pressure pulse waves detected by the pressure detecting elements included in the pressure pulse wave detector.

Accordingly, it is possible to provide a pressure pulse wave detector that can flexibly change a contact state between a living body part and pressure detecting elements to be brought into contact with the living body part, so as to improve detection accuracy of pressure pulse waves, and a biometric information measurement device including the pressure pulse wave detector.

The present invention is effective and user-friendly particularly in application to a blood pressure monitor or the like.

Although the present invention has been described with reference to the specific embodiment, the present invention is not limited to the embodiment, and various changes can be made without departing from the technical concept of the disclosed invention.

The invention claimed is:

1. A pressure pulse wave detector comprising:
a pressing member which includes a pressing face, the pressing face including a plurality of element arrays arranged along a first direction, each of the element arrays including a plurality of pressure detecting elements arranged in a second direction that intersects the first direction;
a pressing mechanism which is configured to press the pressing face against a body surface of a living body where the second direction intersects with an extension direction of an artery under the body surface;
a support member which supports the pressing mechanism and the pressing member;
a housing which is adapted to be attached to a measurement subject, the housing including the support member therein; and
a movement mechanism which is configured to move the support member in the second direction inside the housing by a manual operation,
wherein the pressing face is configured to be rotated around each of two axes which are perpendicular to a pressing direction of the pressing face pressed by the pressing mechanism, the two axes including a first axis extending in the second direction and a second axis perpendicular to the second direction,
wherein the movement mechanism includes:
a slit which extends in the second direction; and
a fixation member including a protrusion which penetrates the slit, is fixed to the support member, and which enables an operation for moving the support member in the second direction, and
wherein the housing includes an upper surface and a pair of end surfaces on opposite sides of the upper surface, one of the end surfaces facing towards a hand of the measurement subject in a state where the housing is attached to the wrist and another of the end surfaces facing away from the hand of the measurement subject in the state where the housing is attached to the wrist, the slit being formed in the another of the end surfaces.

2. A pressure pulse wave detector according claim 1, wherein the movement mechanism further includes:
a spring fixed to the support member;
a slide member having a protrusion and fixed to the support member via the spring; and
a slide rail formed in the housing,
wherein the slide rail including a plurality of recesses, the protrusion of the slide member being configured to engage with any one of the recesses.

3. A biometric information measurement device comprising:
the pressure pulse wave detector according to claim 1; and
a biometric information calculating portion which is configured to calculate biometric information based on pressure pulse waves detected by the pressure detecting elements included in the pressure pulse wave detector.

* * * * *